US009259271B2

(12) United States Patent
Anvari et al.

(10) Patent No.: US 9,259,271 B2
(45) Date of Patent: Feb. 16, 2016

(54) AUTOMATED IN-BORE MR GUIDED ROBOTIC DIAGNOSTIC AND THERAPEUTIC SYSTEM

(76) Inventors: Mehran Anvari, Hamilton (CA); Lianne Stefurak, Milton (CA); Tim Reedman, Georgetown (CA); Timothy Scott Fielding, Mississauga (CA); Michael Richard Max Schmidt, Georgetown (CA); Kevin John Randall, Hamilton (CA); Julian Dobranowski, Dundas (CA); Colm Boylan, Dundas (CA); Lawrence Qi Chao Lee, Toronto (CA); Kevin Warren Morency, Toronto (CA)

( * ) Notice: Subject to any disclaimer, the term of this patent is extended or adjusted under 35 U.S.C. 154(b) by 583 days.

(21) Appl. No.: 13/512,198

(22) PCT Filed: Nov. 26, 2010

(86) PCT No.: PCT/CA2010/001865
§ 371 (c)(1),
(2), (4) Date: Mar. 7, 2013

(87) PCT Pub. No.: WO2011/063511
PCT Pub. Date: Jun. 3, 2011

(65) Prior Publication Data
US 2013/0158565 A1 Jun. 20, 2013

Related U.S. Application Data

(60) Provisional application No. 61/264,761, filed on Nov. 27, 2009, provisional application No. 61/334,851, filed on May 14, 2010.

(51) Int. Cl.
*A61B 19/00* (2006.01)
*A61B 10/02* (2006.01)
(Continued)

(52) U.S. Cl.
CPC ............ *A61B 19/00* (2013.01); *A61B 10/0266* (2013.01); *A61B 19/20* (2013.01);
(Continued)

(58) Field of Classification Search
CPC ...... A61B 19/20; A61B 19/22; A61B 19/201; A61B 19/2203; A61B 19/5244; A61B 2019/207
USPC .............. 606/1, 129, 130, 185, 362; 600/562, 600/417, 424, 429; 901/14–29; 74/490.01–490.09
See application file for complete search history.

(56) References Cited

U.S. PATENT DOCUMENTS 5,460,182 A 10/1995 Goodman et al.
5,749,362 A 5/1998 Funda et al.
(Continued)

FOREIGN PATENT DOCUMENTS

EP 1 791 070 A2 5/2007
EP 1 791 070 B1 5/2007
(Continued)

OTHER PUBLICATIONS

International Preliminary Examiniation Report PCT/CA2010/001865 issued May 30, 2012.
(Continued)

*Primary Examiner* — Todd E Manahan
*Assistant Examiner* — Charles Wei
(74) *Attorney, Agent, or Firm* — Roberts Mlotkowski Safran & Cole P.C.

(57) ABSTRACT

A medical insertion device which may be used with or installed within an imaging system, such as magnetic resonance imaging (MRI). The medical insertion device can generally be used to retain, position and effect insertion of a medical instrument, for example a biopsy device or an ablation treatment device. The device can generally provide linear and/or angular degrees of freedom for positioning of the medical instrument prior to an insertion of the medical instrument. The medical insertion device includes a mounting arm, an interface connected to the mounting arm for interfacing with a medical instrument, a mechanism for movement of the medical instrument or a part of the medical instrument in an insertion direction, a carriage connected to a distal end of the mounting arm, and a pivot connection between the carriage and the distal end of the mounting arm to permit pitch or yaw of the mounting arm.

19 Claims, 21 Drawing Sheets

(51) Int. Cl.
*A61B 17/34* (2006.01)
*A61B 18/02* (2006.01)
*A61B 18/14* (2006.01)
*A61B 18/24* (2006.01)
*A61B 17/00* (2006.01)

(52) U.S. Cl.
CPC ......... *A61B19/2203* (2013.01); *A61B 17/3468* (2013.01); *A61B 18/02* (2013.01); *A61B 18/1477* (2013.01); *A61B 18/24* (2013.01); *A61B 19/201* (2013.01); *A61B 19/5244* (2013.01); *A61B 2017/00911* (2013.01); *A61B 2018/1425* (2013.01); *A61B 2019/205* (2013.01); *A61B 2019/2207* (2013.01); *A61B 2019/2223* (2013.01); *A61B 2019/2292* (2013.01); *A61B 2019/507* (2013.01); *A61B 2019/5236* (2013.01); *A61B 2019/5287* (2013.01); *A61B 2019/5289* (2013.01); *A61B 2019/5454* (2013.01)

(56) References Cited

U.S. PATENT DOCUMENTS

| | | | | |
|---|---|---|---|---|
| 5,828,197 | A * | 10/1998 | Martin et al. | 318/567 |
| 6,064,904 | A | 5/2000 | Yanof et al. | |
| 6,099,217 | A * | 8/2000 | Wiegand | B23Q 1/5462 408/234 |
| 6,351,662 | B1 | 2/2002 | Franck et al. | |
| 6,451,027 | B1 | 9/2002 | Cooper et al. | |
| 6,718,196 | B1 | 4/2004 | Mah et al. | |
| 6,723,106 | B1 * | 4/2004 | Charles et al. | 606/130 |
| 6,955,671 | B2 | 10/2005 | Uchikubo | |
| 6,960,052 | B2 * | 11/2005 | Lutz | B23Q 1/56 409/201 |
| 6,974,297 | B2 * | 12/2005 | Brog.ang.rdh | B23Q 1/5462 414/680 |
| 7,124,660 | B2 * | 10/2006 | Chiang | A47B 91/16 74/490.05 |
| 7,155,316 | B2 * | 12/2006 | Sutherland et al. | 700/248 |
| 7,789,875 | B2 * | 9/2010 | Brock et al. | 606/1 |
| 7,909,303 | B2 * | 3/2011 | Bergmann | B23Q 1/5462 248/605 |
| 8,303,238 | B2 * | 11/2012 | Thurneysen | B23Q 1/4852 414/680 |
| 2002/0077543 | A1 * | 6/2002 | Grzeszczuk et al. | 600/424 |
| 2002/0143319 | A1 * | 10/2002 | Brock | 606/1 |
| 2003/0199754 | A1 | 10/2003 | Hibner et al. | |
| 2007/0021738 | A1 | 1/2007 | Hasser et al. | |
| 2008/0004632 | A1 * | 1/2008 | Sutherland et al. | 606/130 |
| 2009/0192519 | A1 * | 7/2009 | Omori | 606/130 |
| 2009/0248036 | A1 * | 10/2009 | Hoffman et al. | 606/130 |

FOREIGN PATENT DOCUMENTS

| | | |
|---|---|---|
| EP | 1 857 059 A1 | 11/2007 |
| WO | 98/33451 A1 | 8/1998 |
| WO | 2007064937 A1 | 6/2007 |
| WO | 2008/045827 A2 | 4/2008 |
| WO | 2008/109247 A1 | 9/2008 |

OTHER PUBLICATIONS

International Search Report for International Application No. PCT/CA2009/000076 Mailing Date May 12, 2009.
International Preliminary Report on Patentability for International Application No. PCT/CA2009/000076 Date of Issuance of This Report Jul. 27, 2010.
International Search Report PCT/CA2010/001865 mailed Mar. 7, 2011.
Office Action issue in U.S. Appl. No. 13/859,336 dated Jul. 2, 2015.

* cited by examiner

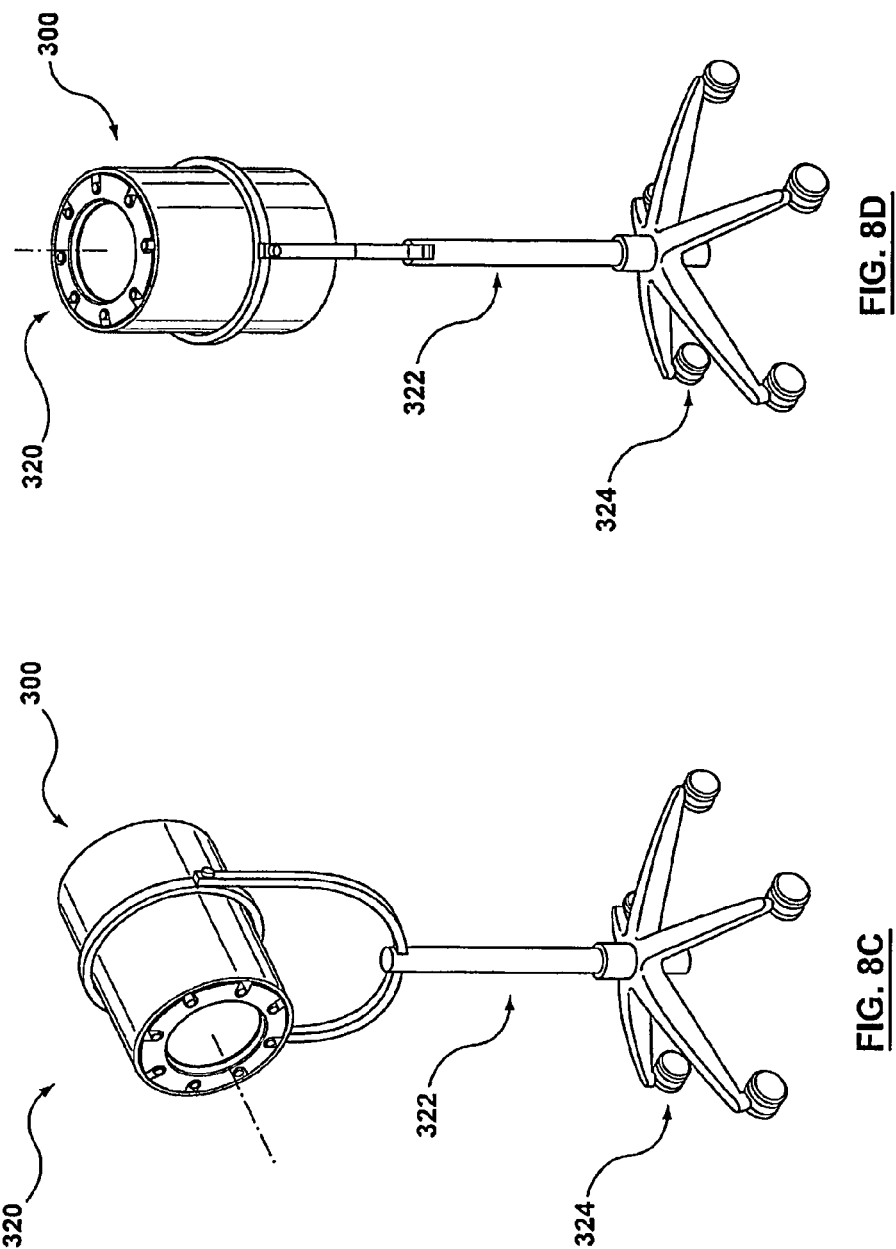

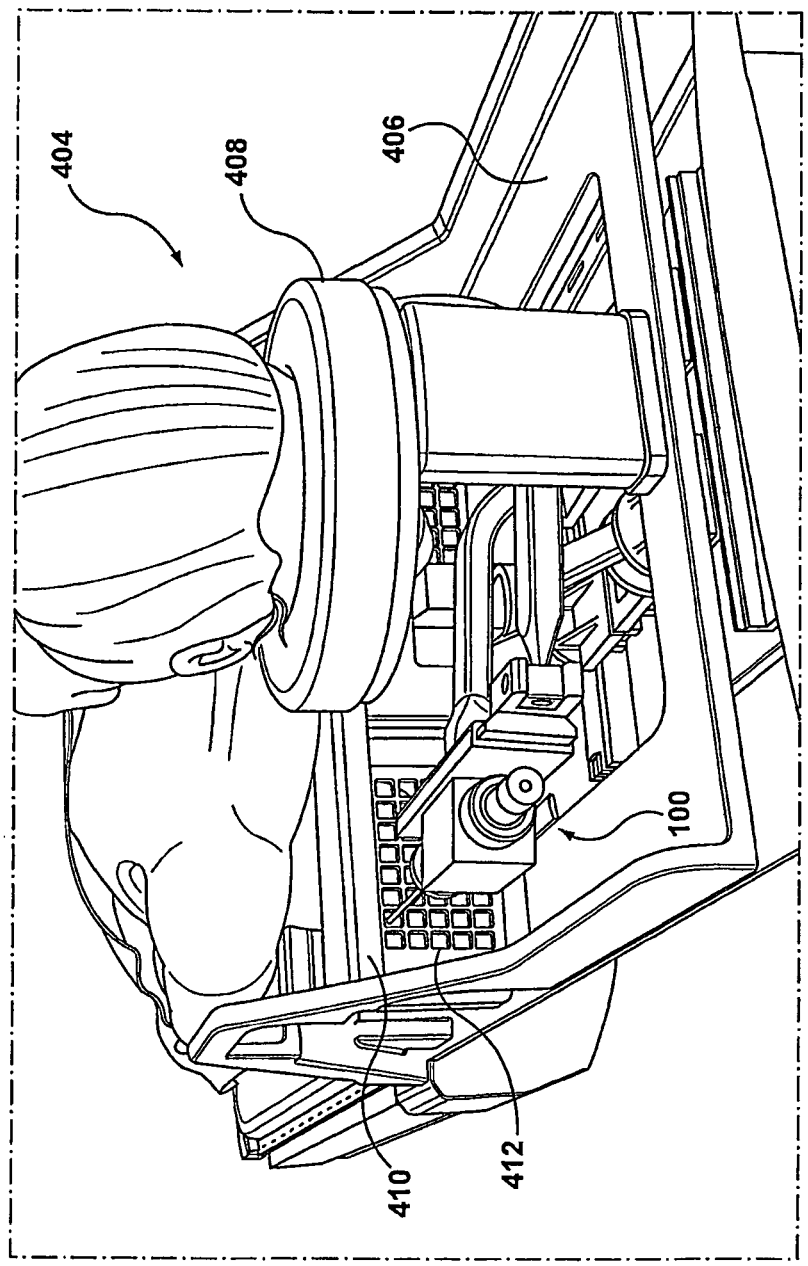

AUTOMATED IN-BORE MR GUIDED ROBOTIC DIAGNOSTIC AND THERAPEUTIC SYSTEM

CROSS-REFERENCE

This application claims the benefit of U.S. Provisional Patent Application No. 61/264,761 filed Nov. 27, 2009 and U.S. Provisional Patent Application No. 61/334,851 filed May 14, 2010, the contents of which are hereby incorporated by reference.

FIELD

Some example embodiments described herein relate to surgical robotics, and in particular to control of medical instruments which have an insertion action, such as a biopsy needle or ablation tool.

BACKGROUND

Cancer diagnosis and treatment can require the medical practitioner to be able to pin point a suspicious lesion within the patient. After the area is located, the next step in a typical treatment process can include a biopsy procedure to identify the pathology, which can be performed in the operating room, with the patient under general anesthetic. In other instances, biopsy procedures can include the implementation of core needle biopsy procedures using minimally invasive core needle extraction methods.

Difficulties can arise in performing of a conventional procedure. As an example, for breast biopsy with magnetic resonance imaging (MRI) systems, the patient may have to be shuttled in and out of the magnet several times before a biopsy is actually performed. During this time, the contrast agent could have already lost some of its effect and image quality could suffer. This process itself may be time consuming and cumbersome, especially in a time-sensitive environment.

In addition, contrast laden blood from a hematoma as well as an air pocket at the biopsy site can make it difficult to subsequently verify that the correct site identified from the imaging system was biopsied, or to rapidly confirm that the sample obtained has a suspect morphology. This practice could also require removal of a relatively large volume of tissue, with a fraction of that assumed to be from the lesion.

SUMMARY

It would be advantageous to provide a medical insertion device which may be used within an imaging system in real-time or near real-time.

Example embodiments relate to a medical insertion device which may be used with or installed within an imaging system, such as a magnetic resonance imaging (MRI) system to plan the best approach to the target tissue. The medical insertion device can generally be used to retain, position and effect insertion of a medical instrument, for example a biopsy device or an ablation treatment device. The device can generally provide linear, rotational and/or angular degrees of freedom for positioning of the medical instrument prior to an insertion of the medical instrument. Embodiments include performance in real-time imaging environment (i.e. "in-bore" imaging). Additional embodiments include data/software integration into the system, allowing a user to pull images taken and employ a 2D or 3D target planning algorithm to provide co-ordinates for device positioning.

In an example embodiment, there is provided a robotic system, including an insertion device having an interface for interfacing with a medical instrument, one or more mechanisms for effecting insertion of the medical instrument or a part of the medical instrument in an insertion direction, and for effecting pitch and yaw of the insertion device, and a controller in communication with the detector subsystem and configured to automatically control the one or more mechanisms based on the received spatial information.

In another example embodiment, there is provided a medical insertion device which includes a mounting arm, an interface connected to the mounting arm for interfacing with a medical instrument, a mechanism for movement of the medical instrument or a part of the medical instrument in an insertion direction, a carriage connected to a distal end of the mounting arm, and a pivot connection between the carriage and the distal end of the mounting arm to permit pitch or yaw of the mounting arm.

In another example embodiment, there is provided a method for facilitating insertion of a medical instrument, which includes: interfacing the medical instrument with an interface, the interface being connected to a mounting arm, pivoting the mounting arm at a pivot connection connected between a carriage and a distal end of the mounting arm to effect pitch or yaw of the mounting arm, and moving the medical instrument or a part of the medical instrument in an insertion direction.

In another example embodiment, there is provided a dispenser system for use with an imaging system, which includes a dispenser frame adjoined to the imaging system, the dispenser frame including or defining at least one instrument holder for holding and releasably providing of a medical instrument.

BRIEF DESCRIPTION OF THE DRAWINGS

Reference will now be made, by way of example, to the accompanying drawings which show example embodiments, and in which:

FIG. 8C shows an isometric view of a dispenser assembly in accordance with another example embodiment in a lateral mode of dispensing;

FIG. 8D shows an isometric view of the dispenser assembly shown in FIG. 8C in an upper mode of dispensing;

FIG. 9C shows a detail isometric view of the robotic surgical system shown in FIG. 9A in another mode of operation.

Similar reference numerals may be used in different figures to denote similar components.

DETAILED DESCRIPTION OF EXAMPLE EMBODIMENTS

Cancer diagnosis or procedures can include using a biopsy tool to retrieve a tissue sample for further analysis. A difficulty with some existing medical systems is that the health practitioner may not be able to work within a CT or MRI system during scanning for procedures such as biopsy or ablation therapy.

Many imaging systems may also have limited space constraints for placement of robotic systems.

Some example embodiments relate to an image guided, automated surgical robotic system having a manipulator, and associated workstations for the purpose of obtaining a biopsy sample and/or treating an identified lesion/pathology. The system can interface with existing clinical diagnostic imaging systems such as magnetic resonance imaging (MRI) to help chose a specific target and then automatically or semi-automatically drive a medical instrument such as a percutaneous coring needle biopsy device or ablation tool, under real-time or near-real-time image guidance.

In an example embodiment, there is provided a robotic system, including an insertion device having an interface for interfacing with a medical instrument, one or more mechanisms for effecting insertion of the medical instrument or a part of the medical instrument in an insertion direction, and for effecting pitch and yaw of the insertion device, a detector subsystem for determining spatial information, and a controller in communication with the detector subsystem and configured to automatically control the one or more mechanisms based on the received spatial information.

In another example embodiment, there is provided a medical insertion device which includes a mounting arm, an interface connected to the mounting arm for interfacing with a medical instrument, a mechanism for movement of the medical instrument or a part of the medical instrument in an insertion direction, a carriage connected to a distal end of the mounting arm, and a pivot connection between the carriage and the distal end of the mounting arm to permit pitch or yaw of the mounting arm.

In another example embodiment, there is provided a method for facilitating insertion of a medical instrument, or the use of the medical instrument, which includes: interfacing the medical instrument with an interface, the interface being connected to a mounting arm, pivoting the mounting arm at a pivot connection connected between a carriage and a distal end of the mounting arm to effect pitch or yaw of the mounting arm, and moving the medical instrument or a part of the medical instrument in an insertion direction.

In another example embodiment, there is provided a dispenser system for use with an imaging system, which includes a dispenser frame adjoined to the imaging system, the dispenser frame including or defining at least one instrument holder for holding and releasably providing of a medical instrument.

Figure 1A:
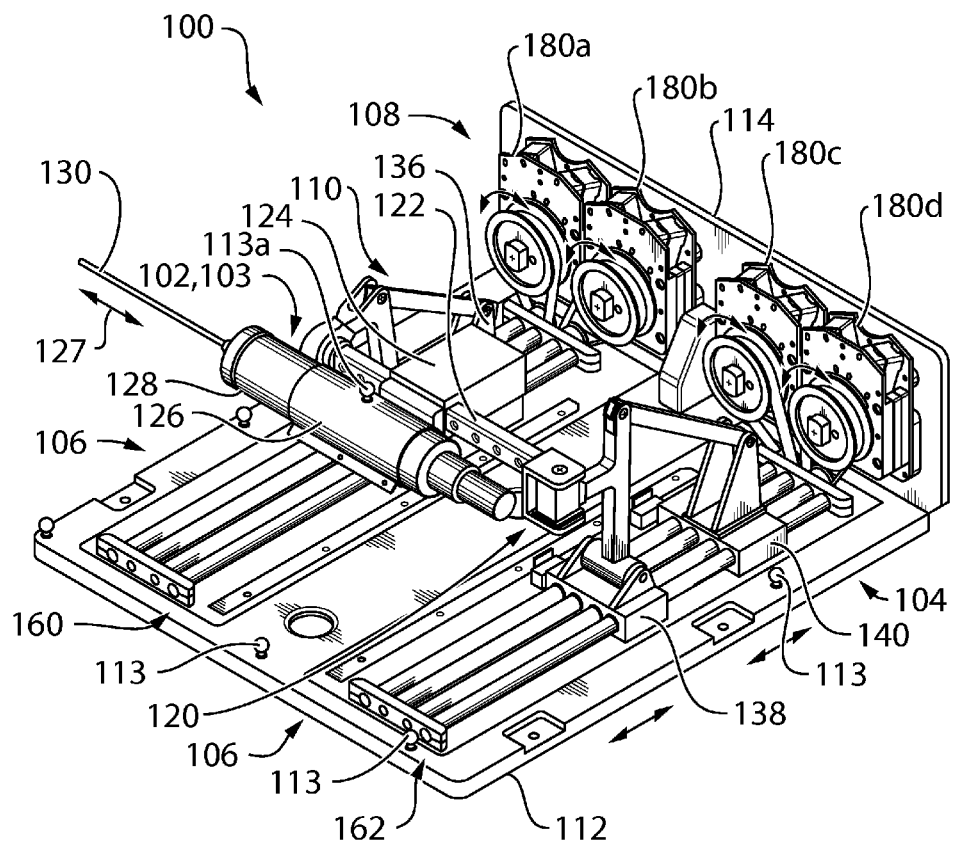
FIG. 1A shows an isometric view of a medical insertion device in accordance with an example embodiment.
Figure 1B:
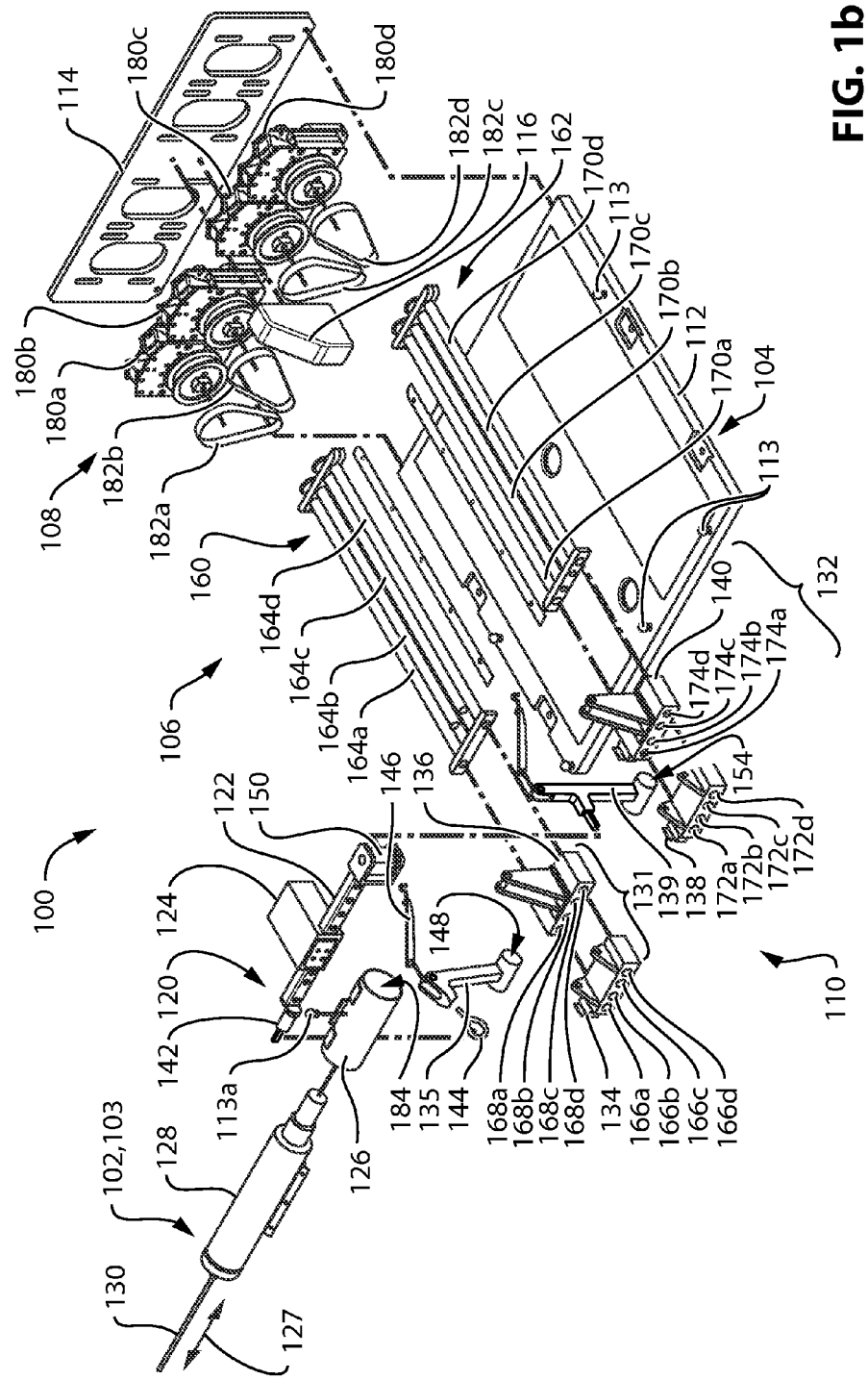
FIG. 1B shows an exploded isometric view of the medical insertion device shown in FIG. 1A.
Figure 1C:
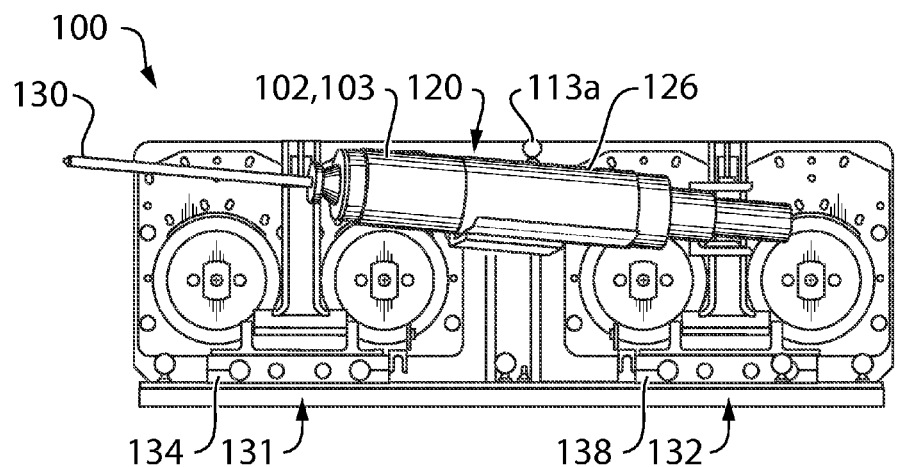
FIG. 1C shows a left side view of the medical insertion device shown in FIG. 1A.
Figure 1D:
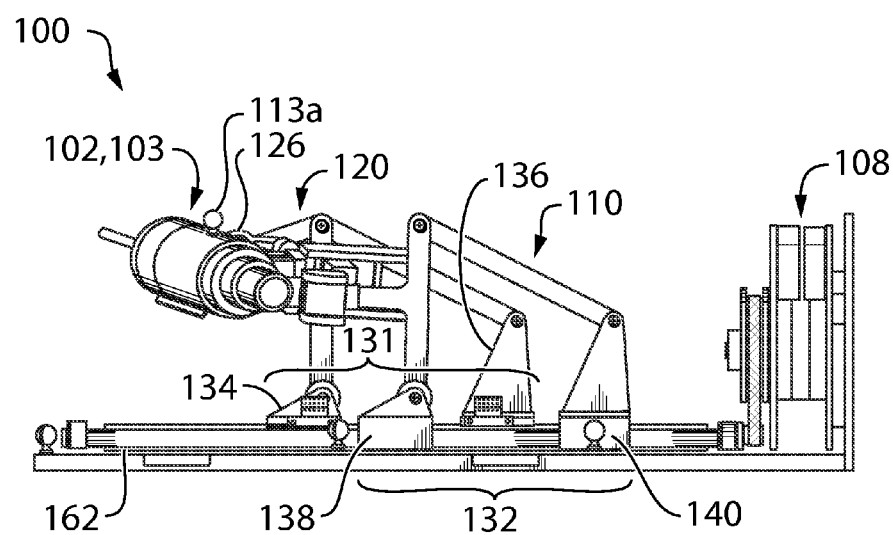
FIG. 1D shows a rear side view of the medical insertion device shown in FIG. 1A.
Figure 1E:
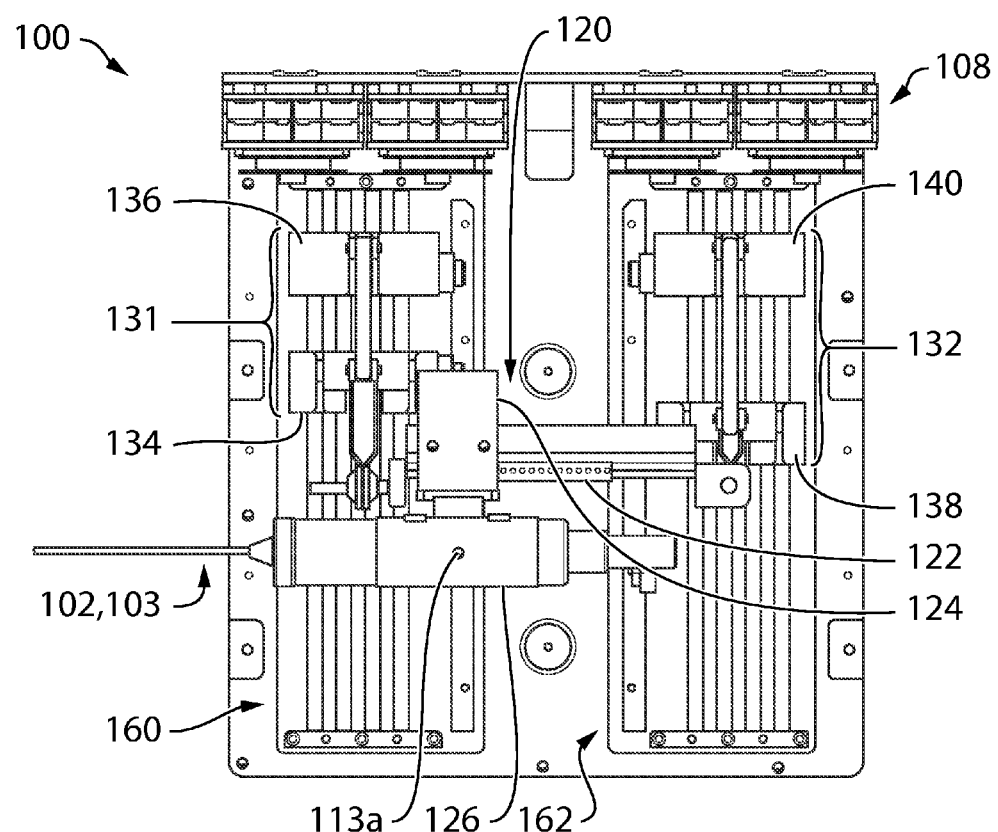
FIG. 1E shows a plan view of the medical insertion device shown in FIG. 1A.

Reference is first made to FIGS. 1A and 1B, which show a medical insertion device 100 in accordance with an example embodiment. Generally, the medical insertion device 100 may be used with or installed within an imaging system (not shown here), such as a magnetic resonance imaging (MRI) system, during scanning. The medical insertion device 100 can generally be used to retain, position and effect insertion of a medical instrument 102, for example a biopsy device 103 as shown, or for example a treatment device. The device 100 can generally provide linear, angular and/or rotational degrees of freedom for positioning of the medical instrument 102 prior to insertion of the medical instrument 102.

As shown in FIG. 1B, the medical insertion device 100 includes a frame 104 which acts to house the medical insertion device 100. The medical insertion device 100 further includes a linear slide assembly 106 mounted or connected to the frame 104. The medical insertion device further includes a rotary drive assembly 108 for generally driving the linear slide assembly 106, and a carriage assembly 110 for moving along the linear slide assembly 106. The carriage assembly 110 also generally supports the medical instrument 102 for positioning and insertion thereof.

Referring still to FIG. 1B, the frame 104 will now be described in greater detail. The frame 104 includes a baseplate 112 and a drive support plate 114 connected thereto to at least partially form a housing of the medical insertion device 100. Other sidewalls or plates (not shown) may also form part of the frame 104. The frame 104 also includes a drive plate strengthening bracket 116 for strengthening of the connection between the baseplate 112 and the drive support plate 114. Other strengthening brackets (not shown) may also be used. The baseplate 112 may also include alignment fiducials 113 or other alignment markers for correlating the physical world with an imaging system (not shown here). An additional alignment fiducial 113a or fiducials may be placed on the elongate mounting arm 120 (e.g. device holder 126), or on the medical instrument 102 itself (not shown), for correlating or registration purposes. In some example embodiments, the alignment fiducials can include MR molecular tagging. In some example embodiments, the frame 104 encloses almost an entirety of the medical insertion device 100, save for the frame 104 further including or defining an opening at the front for passage of the medical instrument 102 there through. In yet further embodiments, the frame 104 is integrated into or forms part of a same frame (not shown here) of the particular imaging system (not shown here). The frame 104 can be panel shaped to fit within restricted environments having a limited height.

Referring still to FIG. 1B, the carriage assembly 110 includes an elongate mounting arm 120, wherein the mounting arm 120 includes an insertion track 122 which runs along a length of the mounting arm 120. An insertion carriage 124 includes a mechanism such as a pneumatic or piezoelectric motor which can move or step the carriage 124 along the insertion track 122. The insertion carriage 124 is therefore slideably mounted to the insertion track 122. A device holder 126 is connected to the carriage 124. The device holder 126 is generally tubular shaped and acts as an interface to receive or interface with the medical instrument 102. As shown in FIG. 1B, the device holder 126 includes a sheath to receive a corresponding tubular-shaped main body 128 of the medical instrument 102. Thus, movement of the insertion carriage 124 along the insertion track 122 causes the medical instrument 102 to move in an insertion direction 127. In the example shown, the mounting arm 120 also defines the insertion direction 127. In some example embodiments, the mounting arm 120 and/or the device holder 126 includes a force sensor(s) to detect the tissue being penetrated, and for prevention of accidental excursion into the incorrect tissue (e.g. chest wall).

Referring still to FIG. 1B, the medical instrument 102 typically includes the main body 128 and an elongate member 130 such as a needle which extends from the main body 128. In example embodiments, the elongate member 130 is formed from MR compatible materials such as carbon fibre, ceramic, or tritanium. One example of the medical instrument 102 is a biopsy tool 103, such as a vacuum assisted biopsy (VAB) device available from ATEC™, as would be understood in the art. The elongate member 130 can also include an ablative tool such as Radio Frequency (RF) ablation, focused ultrasound, cryotherapy, laser and other ablative technologies that are administered within the cancerous region causing cell destruction with minimal damage to surrounding tissues. In some example embodiments, the medical instrument 102 may also include a detector such as a probe, ultrasound probe, or fiber optic probe. The detector can also include an MRI coil to provide higher resolution in situ imaging. In yet further example embodiments, the medical instrument 102 may be integrated with the device holder 126 to result in a dedicated-purpose insertion device. In yet further example embodiments, the medical instrument 102 can include an end effector or end effectors.

Figure 2:
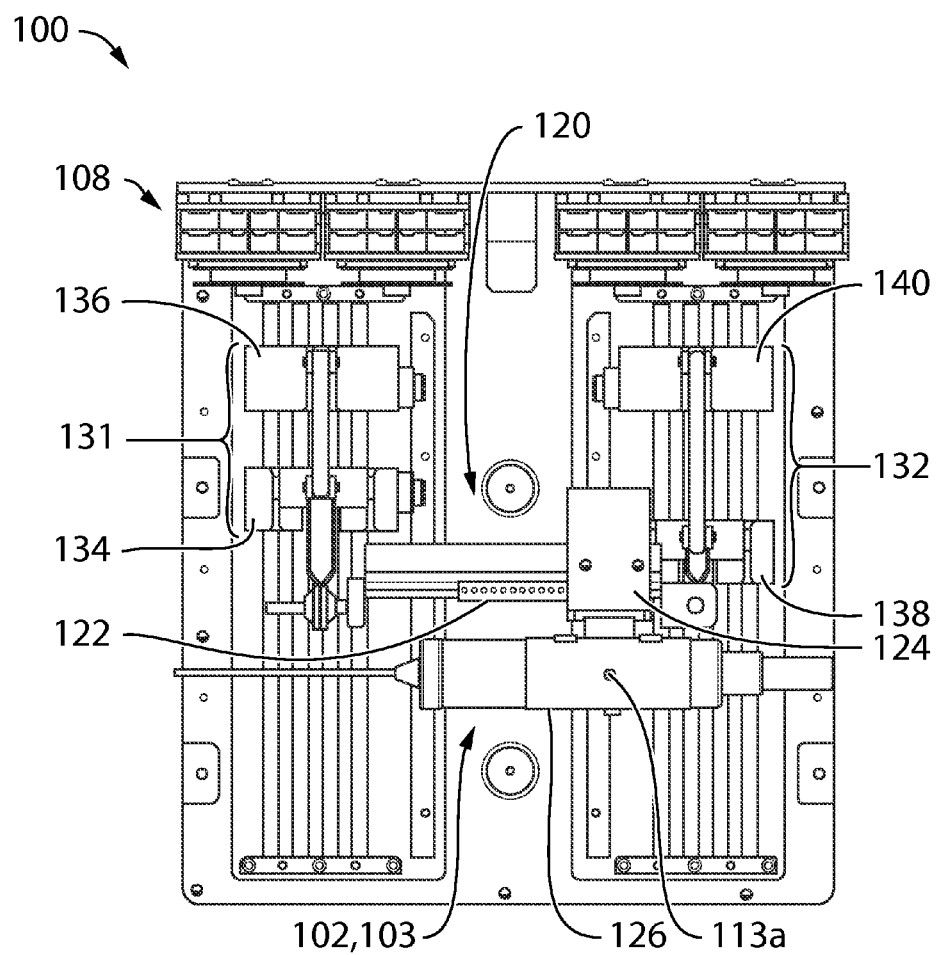
FIG. 2 shows an isometric view of the medical insertion device in a retraction configuration.

Reference is now made to FIG. 2, which shows the medical instrument 102 in a retraction configuration or orientation. As shown, the insertion carriage 124 is located at a proximal end of the insertion track 122, which therefore has retracted the medical instrument 102 backwards along the insertion direction 127 (with respect to FIG. 1A). From this position, the insertion carriage 124 can move along the insertion track 122 to the distal end of the insertion track 122, resulting in the medical instrument 102 moving in the insertion direction 127 to an insertion configuration or orientation as shown in FIG. 1A.

In example embodiments, referring again to FIG. 1B, the carriage assembly 110 generally includes one or more carriages which including pivot connections and/or slideable connections for effecting positioning of the mounting arm 120, and therefore positioning of the medical instrument 102. Once at the desired position, the next step is typically an insertion step through the skin which includes movement of the insertion carriage 124 along the insertion track 122 in the insertion direction 127.

In the example shown in FIG. 1B, the carriage assembly 110 includes a first carriage coupling 131 and a second carriage coupling 132. The first carriage coupling 131 includes a first carriage 134 and a second carriage 136. The second carriage coupling 132 includes a third carriage 138 and a fourth carriage 140. As shown, the first carriage 134 via first sway arm 135 is connected to a distal end of the mounting arm 120 using a ball-and-socket pivot connection, which is defined by a ball 142 of the mounting arm 120 and a corresponding socket 144 of the first sway arm 135. Such a pivot connection therefore permits pitch or yaw of the mounting arm 120 in operation. The first carriage 134 also itself includes a pivoting (e.g. hinged) connection 148 with the first sway arm 135 at the linear slide assembly 106. The first sway arm 135 is also hingedly connected to a first coupling arm 146. The first coupling arm 146 is hingedly connected to the second carriage 136.

The third carriage 138 is connected to a proximal end of the mounting arm 120 via a second sway arm 139, using a pivoting connection 150 such as a first hinge coupled with a second hinge, as shown. The second sway arm 139 is hingedly connected to a second coupling arm 152. The second coupling arm 152 is hingedly connected to the fourth carriage 140. The third carriage 138 also includes a pivoting (e.g. hinged) connection 154 to the second sway arm 139 at the linear slide assembly 106.

Referring still to FIG. 1B, the linear slide assembly 106 provides a support for the carriage assembly 110, and includes a first track system 160 and a second track system 162 having mechanisms for individually or collectively controlling of the positioning of the carriages 134, 136, 138, 140. As shown, the first track system 160 supports the first carriage coupling 131 and the second track system 162 supports the second carriage coupling 132. The first and second track systems 160, 162 include straightly moveable or slideable connections with the respective carriages 134, 136, 138, 140 for facilitating linear translation of the carriages 134, 136, 138, 140.

Referring to the first track system 160, this includes four rails 164a-d, which correspond respectively to channels 166a-d defined by the first carriage 134 and channels 168a-d defined by the second carriage 136, as shown in FIG. 1B. In the example embodiment shown, first and fourth rails 164a and 164d are smooth rails which act as guide rails for sliding of the first carriage 134 and the second carriage 136. Thus, channels 166a, 166d, 168a, and 168d may also have smooth inner surfaces. Second rail 164b includes a lengthwise screw thread definition which engages corresponding anti-backlash nut (not shown) within channel 166b of the first carriage 134. Channel 168b of second carriage 136 has a smooth inner surface. Thus, rotation of second rail 164b results in horizontal translation of first carriage 134 while not affecting the second carriage 136. Similarly, third rail 164c includes a lengthwise screw thread definition which engages corresponding anti-backlash nut (not shown) within channel 168c of the second carriage 136. Channel 166c of first carriage 134 has a smooth inner surface. Thus, rotation of the third rail 164c results in horizontal translation of the second carriage 136 along the first rail system 160 while not affecting the first carriage 134.

In example embodiments, a similar configuration may be used for the second track system 162, which includes four rails 170a-d, which correspond respectively to channels 172a-d defined by the third carriage 138 and channels 174a-d defined by the fourth carriage 176, as shown in FIG. 1B. In the example embodiment shown, first and fourth rails 170a and 170d are smooth rails which act as guide rails for sliding of the third carriage 138 and the second carriage 140. Thus, channels 172a, 172d, 174a, and 174d may also have smooth inner surfaces. Second rail 170 includes a lengthwise screw thread definition which engages corresponding screw threads of channel 172b of the third carriage 138. Channel 174b of fourth carriage 140 has a smooth inner surface. Thus, rotation of second rail 170b results in horizontal translation of third carriage 138 while not affecting the fourth carriage 140. Similarly, third rail 170c includes a lengthwise screw thread definition which engages corresponding screw threads of channel 174c of the fourth carriage 140. Channel 172c of third carriage 138 has a smooth inner surface. Thus, rotation of the third rail 170c results in horizontal translation of the fourth carriage 140 along the second rail system 162 while not affecting the third carriage 138.

Referring still to FIG. 1B, reference is now made to the rotary drive assembly 108, which acts to drive the various tracks of the linear slide assembly 106, for driving of the various carriages 134, 136, 138, 140 of the carriage assembly 110. In the example embodiment shown, the rotary drive assembly 108 includes four rotary drive units 180a-d (each or individually referred to as 180) each corresponding to a respective rotary drive belt 182a-d. As shown, rotary drive unit 180a is coupled to rail 164b, rotary drive unit 180b is coupled to rail 164c, rotary drive unit 180c is coupled to rail 170b, and rotary drive unit 180d is coupled to rail 170c.

Figure 3A:
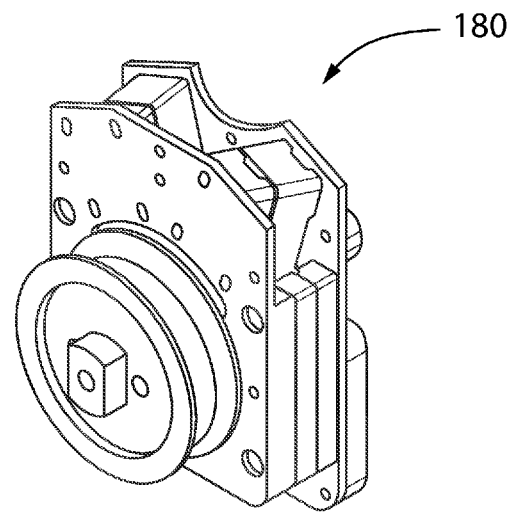
FIG. 3A shows a detail isometric view of a rotary drive unit in accordance with an example embodiment.
Figure 3B:
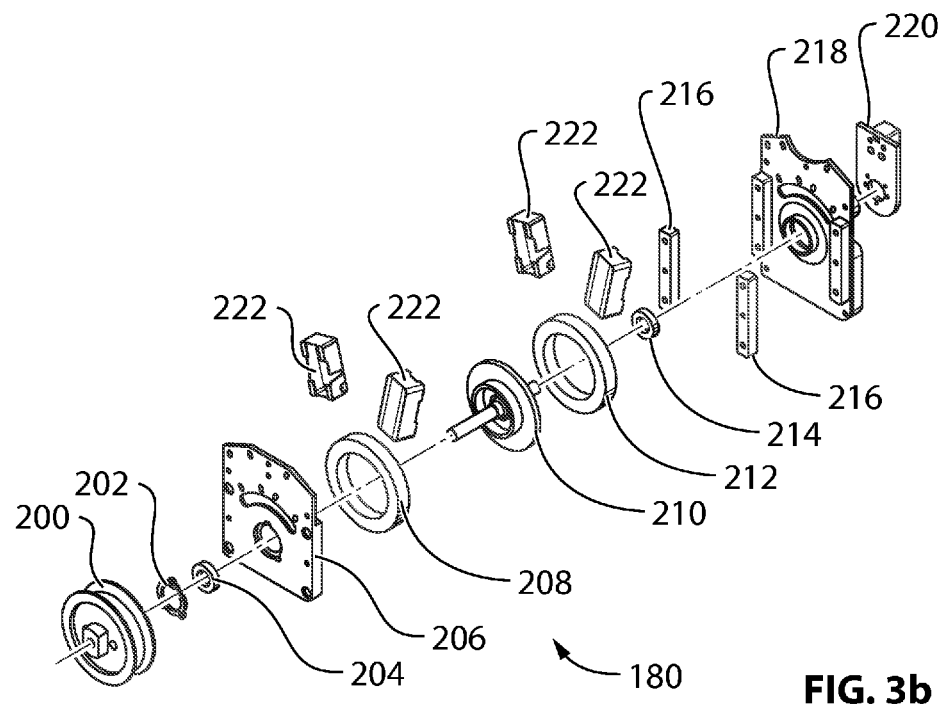
FIG. 3B shows an exploded isometric view of the rotary drive unit shown in FIG. 3A.

Reference is now made to FIGS. 3A and 3B, which show a rotary drive unit 180 in greater detail, in accordance with an example embodiment. As shown in FIG. 3B, the drive unit 180 includes, in sequential adjoining order, a pulley 200 for engaging the drive belt 182a-d, a retaining ring 202, a ceramic bearing 204, a front motor plate 206, a ceramic ring 208, a drive shaft 210, a second ceramic ring 212, a second ceramic bearing 214, one or more spacer plates 216 (two shown), a back motor plate 218, and a controller such as a microcontroller or encoder 220. Four motors such as ultrasonic motors 222 can be used to drive the drive shaft 210, which are controllable by the encoder 220. An example suitable ultrasonic motor 222 is a HR2 motor by Nanomotion Ltd., as would be understood in the art. In other example embodiments, vacuum-actuated drivers or hydraulic drivers may be used.

Referring still to FIG. 1B, various modes of operation of the medical insertion device 100 can be effected to position the medical instrument 102 by slideably moving at least one of the carriages 134, 136, 138, 140. For example, for each carriage coupling 131, 132 the individual carriages may be moved so that relative motion (left or right) between two carriages will raise one end of the mounting arm 120 up or down, either linearly or in a slightly curved trajectory. The slightly curved trajectory also results in axial rotation of the medical instrument 102. Translation of the two carriages couplings 131, 132 in unison results in a linear translation left and right. A differential motion left and right between the first carriage coupling 131 and the second carriage coupling 132 results in a horizontal angular motion (yaw), while a differential vertical motion between the first carriage coupling 131 and the second carriage coupling 132 results in a vertical angle (pitch). Raising or lowering the first carriage coupling 131 and the second carriage coupling 132 in unison results in a combined vertical motion.

Figure 4A:
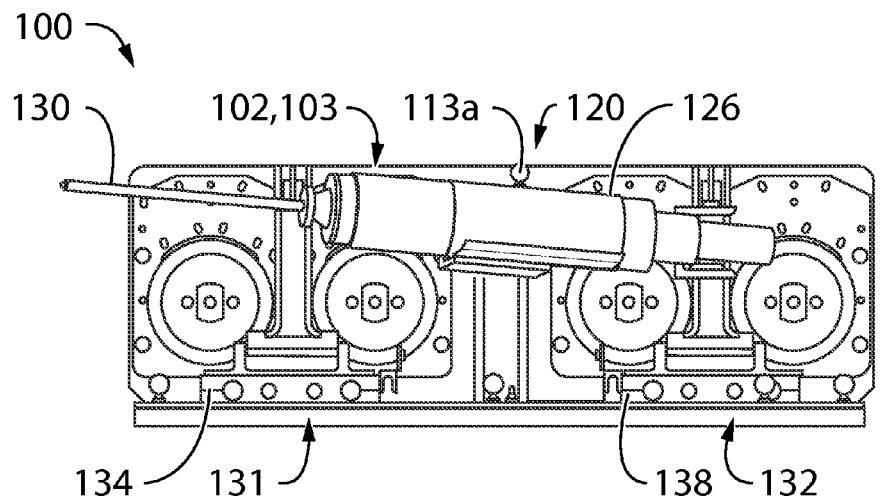
FIG. 4A shows a left side view of the medical insertion device shown in FIG. 1A in a pitch up configuration.
Figure 4B:
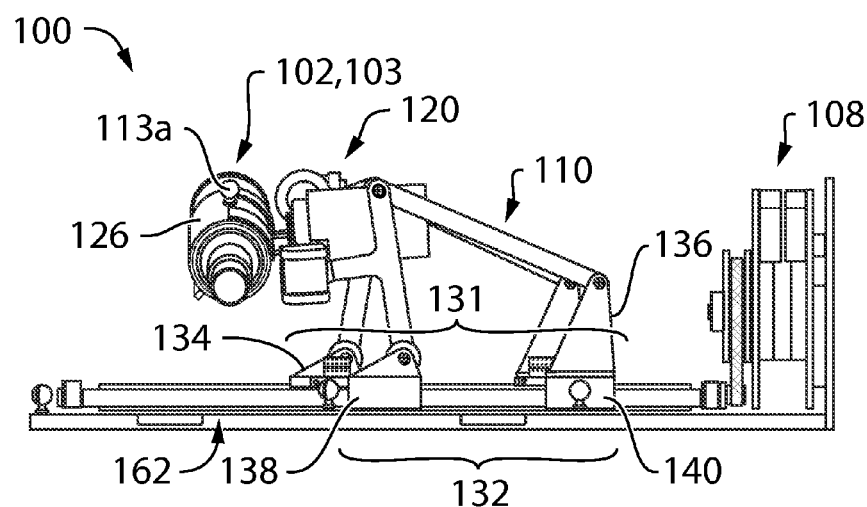
FIG. 4B shows a rear side view of the medical insertion device shown in FIG. 4A in the pitch up configuration.

Reference is thus made to FIGS. 4A and 4B, which show the medical insertion device 100 in a pitch up configuration. As shown, to effect the pitch up configuration, the first carriage 134 and the second carriage 136 are slideably moved relatively towards each other. In some embodiments, only one of the first carriage 134 and the second carriage 136 is moved towards the other, resulting in a slightly curved pitch up trajectory. This slightly curved trajectory also results in axial rotation of the medical instrument 102. In another example embodiment (not shown), a pitch down may be effected by having the first carriage 134 and the second carriage 136 slideably moved relatively away from each other.

Figure 5A:
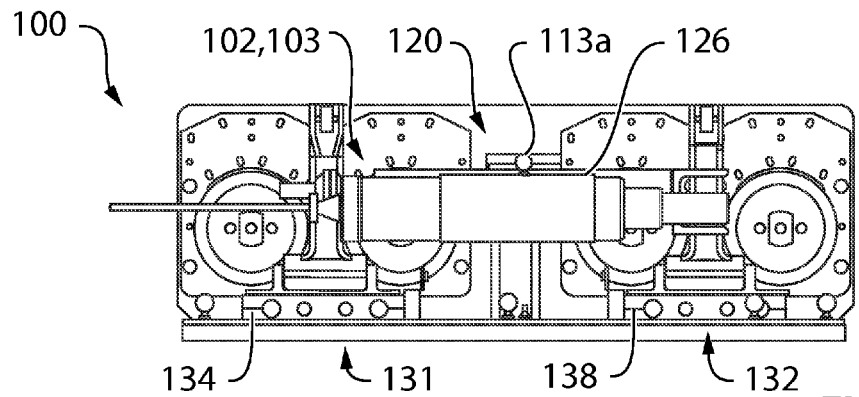
FIG. 5A shows a left side view of the medical insertion device shown in FIG. 1A in a straight insertion configuration.
Figure 5B:
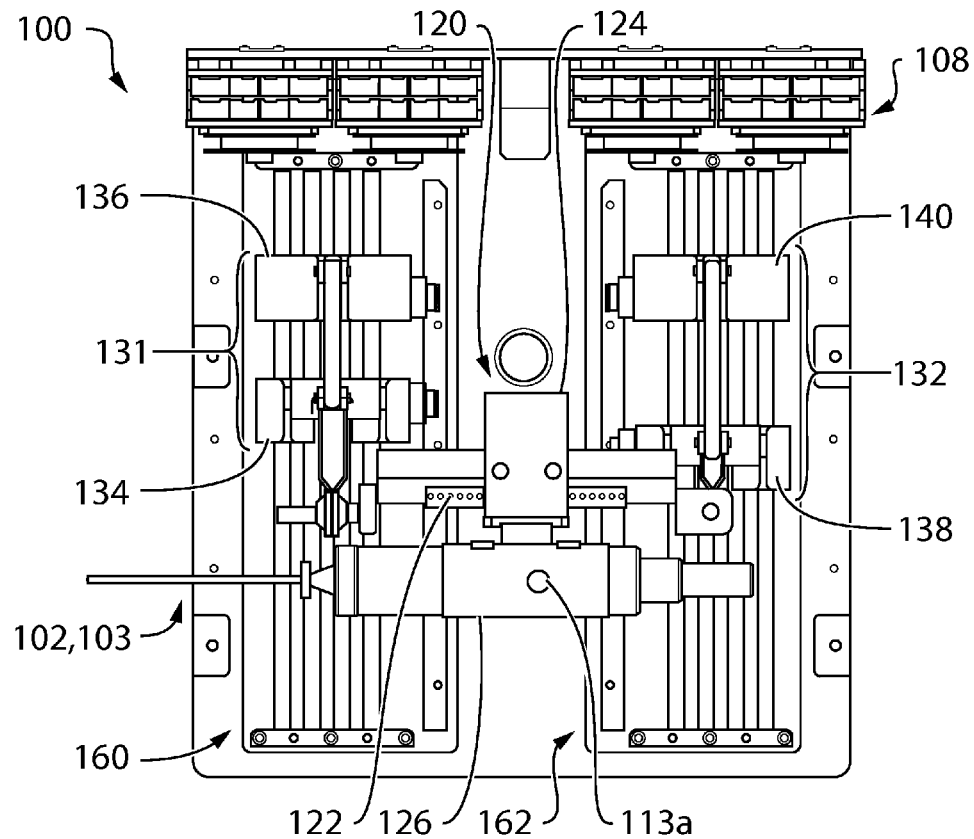
FIG. 5B shows a plan view of the medical insertion device shown in FIG. 5A in the straight insertion configuration.

Reference is also made to FIGS. 5A and 5B, which show the medical insertion device 100 in a straight insertion configuration. As shown, to effect the straight insertion configuration, at least one of the carriages 134, 136, 138, 140 are slideably moved to cause the medical instrument 102 to be horizontally oriented, which would be rectilinear to the insertion target.

Figure 6A:
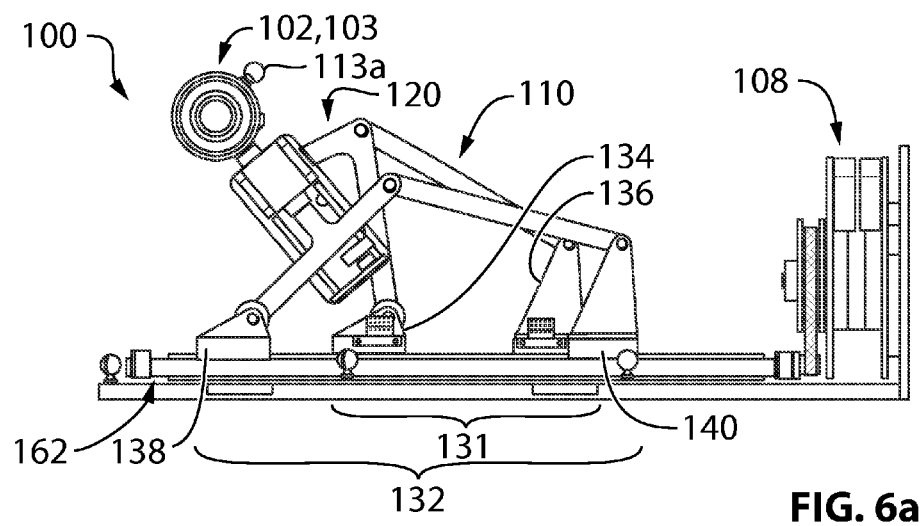
FIG. 6A shows a left side view of the medical insertion device shown in FIG. 1A in a translated configuration.
Figure 6B:
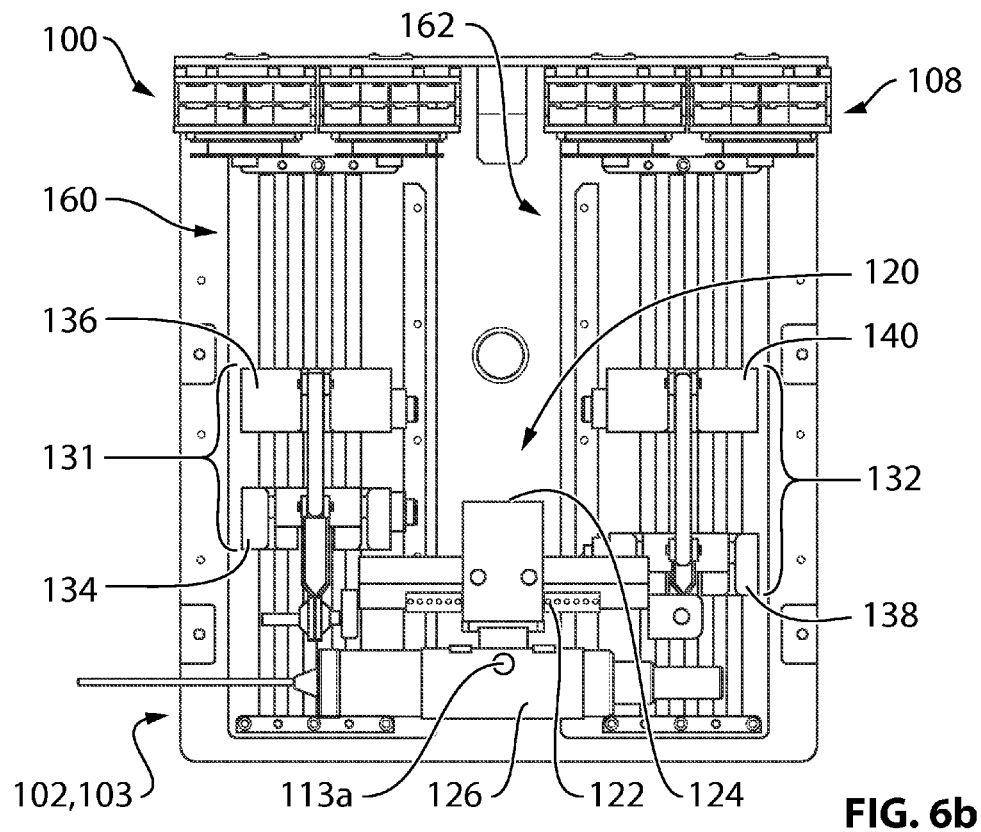
FIG. 6B shows a rear side view of the medical insertion device shown in FIG. 6A in the translated configuration.

Reference is now made to FIGS. 6A and 6B, which show the medical insertion device 100 in a translated configuration. As shown, all of the carriages 134, 136, 138, 140 are slideably moved at the same displacement in a direction, for example left (as shown) or right.

Figure 7A:
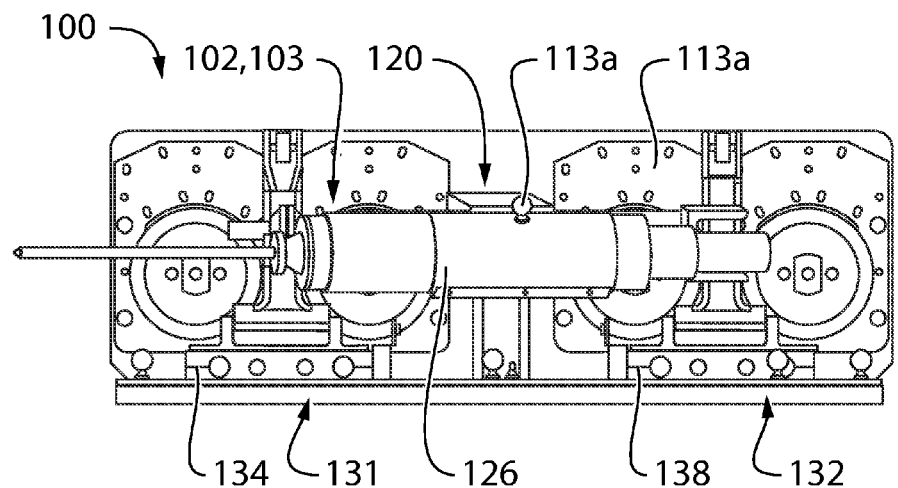
FIG. 7A shows a left side view of the medical insertion device shown in FIG. 1A in a yaw configuration.
Figure 7B:
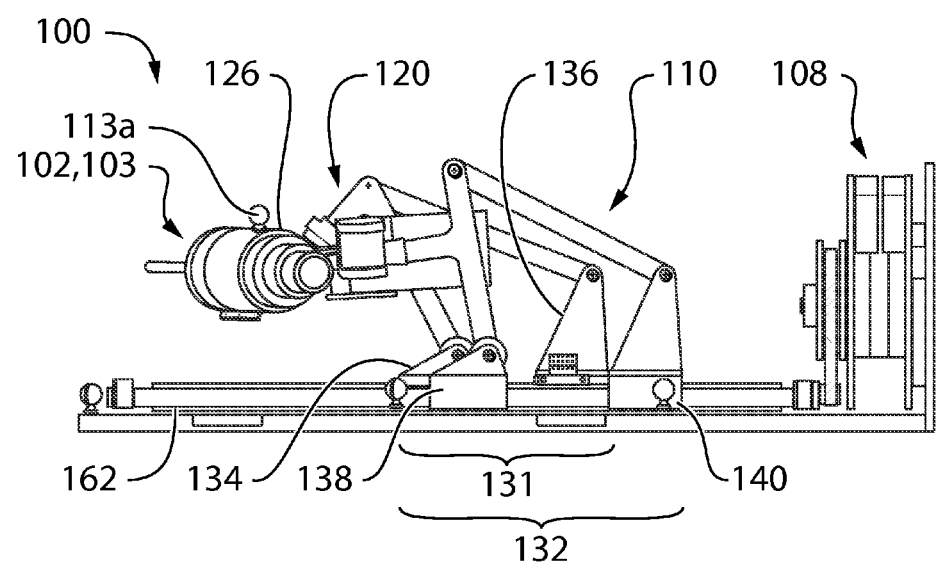
FIG. 7B shows a rear side view of the medical insertion device shown in FIG. 7A in the yaw configuration.
Figure 7C:
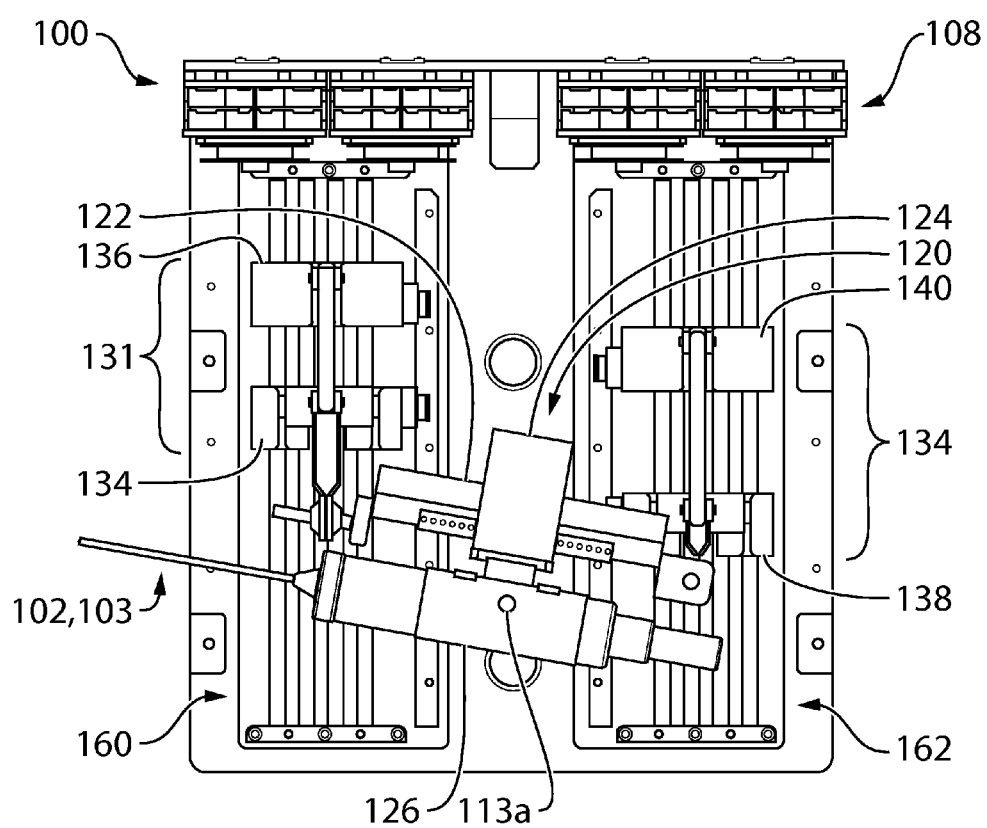
FIG. 7C shows a plan view of the medical insertion device shown in FIG. 7A in the yaw configuration.

Reference is now made to FIGS. 7A, 7B and 7C, which show the medical insertion device 100 in a yaw configuration. As best shown in FIG. 7C, the carriages 138, 140 of the second carriage coupling 132 can be collectively moved leftwardly relative to the first carriage coupling 131 to result in the medical instrument 102 being angled in a yaw right direction. Similarly, the carriages 138, 140 of the second carriage coupling 132 can be collectively moved rightwardly relative to the first carriage coupling 131 to result in the medical instrument 102 being angled in a yaw left direction (not shown).

Referring again to FIG. 1B, it can be appreciated that the medical insertion device 100 can effect various insertion angles of the medical instrument 102 which vary from a straight insertion. It may be appreciated that the various insertion angles may provide flexibility in performing the particular procedure. Further, it may be appreciated that the medical insertion device 100 may provide a stable insertion angle for the subsequent insertion step. In addition, the medical instrument 102 may for example be able to reach additional target regions such as those near the edges of the frame 104 (e.g. at regions beyond the linear slide assembly 106 closer to the baseplate 112).

It may also be appreciated that a difficulty with some existing conventional systems is that conventional articulated or snake-like robotic arms may not be able to provide the required stability or control for performing such a procedure within an imaging system, and especially for the final subcutaneous insertion step of the needle through the skin and tissue.

Referring again to FIG. 1B, in another mode of operation, it can be appreciated that the device holder 126 can be reversed, in that the body 128 of the medical instrument 102 can be inserted into the other opening 184 of the device holder 126. For example, the configuration shown in FIG. 1B may be used for superior (from the head) insertion at the right breast in a "right side" configuration. The entire medical instrument 102 (e.g. the frame 104) can then be reversed with the body 128 of the medical instrument 102 inserted into the other opening 184 of the device holder 126 for superior insertion at the left breast in a "left side" configuration. Of course, in the "left side" configuration the references herein to proximal and distal would be reversed. It may be appreciated that such a reversible configuration could provide operation of the device 100 in a limited space environment such as within an MRI (not shown here).

Suitable materials for the various described assemblies and subsystems of the device 100 include magnetic resonance (MR) compatible materials, ceramics, thermo-plastics and thermo-sets. Additional example materials may also include carbon fiber, ceramic, composites, nanoparticle composites, aluminium, titanium, and stainless steel. Examples of MR compatible motors include piezoelectric motors, pneumatic, vacuum-actuated drivers or hydraulic drivers.

Variations may be made to the device 100 in example embodiments. For example, in some example embodiment, an insertion mechanism may be used to move the entire linear slide assembly 106 in the insertion direction 127 to provide the insertion step (rather than from the insertion track 122). In some additional embodiments, some medical instruments 102 may include their own insertion or injection mechanism, which may be automated or manually controlled. For example, in some example embodiments, only a part of the medical instrument 102 such as the elongate member 130 (e.g. a needle) is independently controllable by a mechanism for insertion.

Figure 8A:
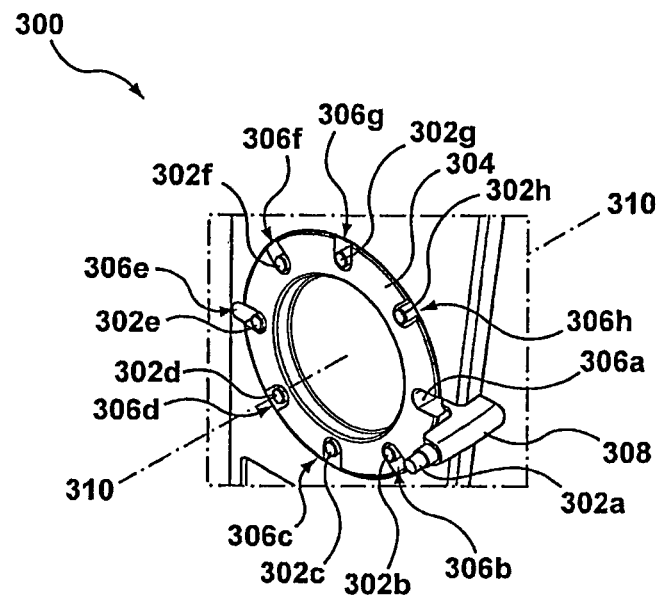
FIG. 8A shows an isometric front view of a dispenser system in accordance with an example embodiment.
Figure 8B:
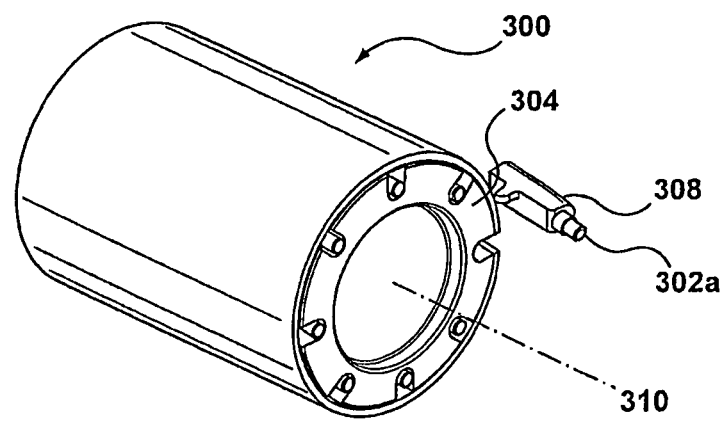
FIG. 8B shows an isometric exploded side view of the dispenser system shown in FIG. 8A.

Reference is now made to FIGS. 8A and 8B, which shows a dispenser system 300 in accordance with an example embodiment. The dispenser system 300 can for example be used with an imaging system (not shown here) to dispense one or more medical instruments 302a-h (each or individually referred to as 302) to the medical insertion device 100 (FIG. 1A). As shown, the dispenser system 300 includes a dispenser frame 304 which can be adjoined or attached to the particular imaging system. The dispenser frame 304 includes or defines a plurality of instrument holders 306a-h (each or individually referred to as 306) for respectively holding the medical instruments 302a-h. The instrument holders 306a-h can also releasably secure the medical instruments 302a-h using a retaining mechanism (not shown).

As shown in FIG. 8A, the dispenser system 300 can also include a receiver 308 which can receive the desired medical instrument 302 for dispensing, in this example medical instrument 302a. The receiver 308 can include a mechanism or a vacuum or air pump (not shown) for obtaining the medical instrument 302a from the particular instrument holder 306a. The receiver 308 can also include appropriate sterilization mechanisms (not shown) such as an alcohol spray, etc.

As shown in FIG. 8A, each instrument holder 306 is arranged on the dispenser frame 304 around a centre of rotation 310 of the dispenser frame 304. The dispenser frame 304 can further include a rotating mechanism (not shown) for rotating of the dispenser frame 304 around the centre of rotation 310. Thus, for example, rotation of the dispenser frame 304 can be effected until the desired medical instrument 302 is aligned with the receiver 308 for dispensing.

In some example embodiments, each of the medical instruments 302a-h can have a universal body which can each interchangeably be used with the medical insertion device 100. In the example embodiments shown, the medical instruments 302a-h can each have a similar elongate cylindrical body for interfacing with a corresponding shape of the device holder 126 (FIG. 1A). It can be appreciated that the dispenser system 300 therefore generally acts as a holster for the medical instruments 302a-h.

Reference is now made to FIGS. 8C and 8D, which show a dispenser assembly 320 in accordance with another example embodiment. FIG. 8C shows a lateral mode of dispensing while FIG. 8D shows an upper mode of dispensing. In the lateral mode (FIG. 8C) the instrument holders 306 are directed laterally (sideways) for accessing of the medical instruments 302. In the upper mode (FIG. 8D) the instrument holders 306 are directed upwardly for accessing of the medical instruments 302. As shown, the dispenser system 300 is mounted onto a stand 322. The stand 322 includes a plurality of wheels 324 (e.g. five), which are lockable once wheeled to the desired position. The stand 322 also includes a swivel mechanism 324, which can swivel and lock the dispenser system 300 between the lateral mode (FIG. 8C) and the upper mode (FIG. 8D).

Figure 9A:
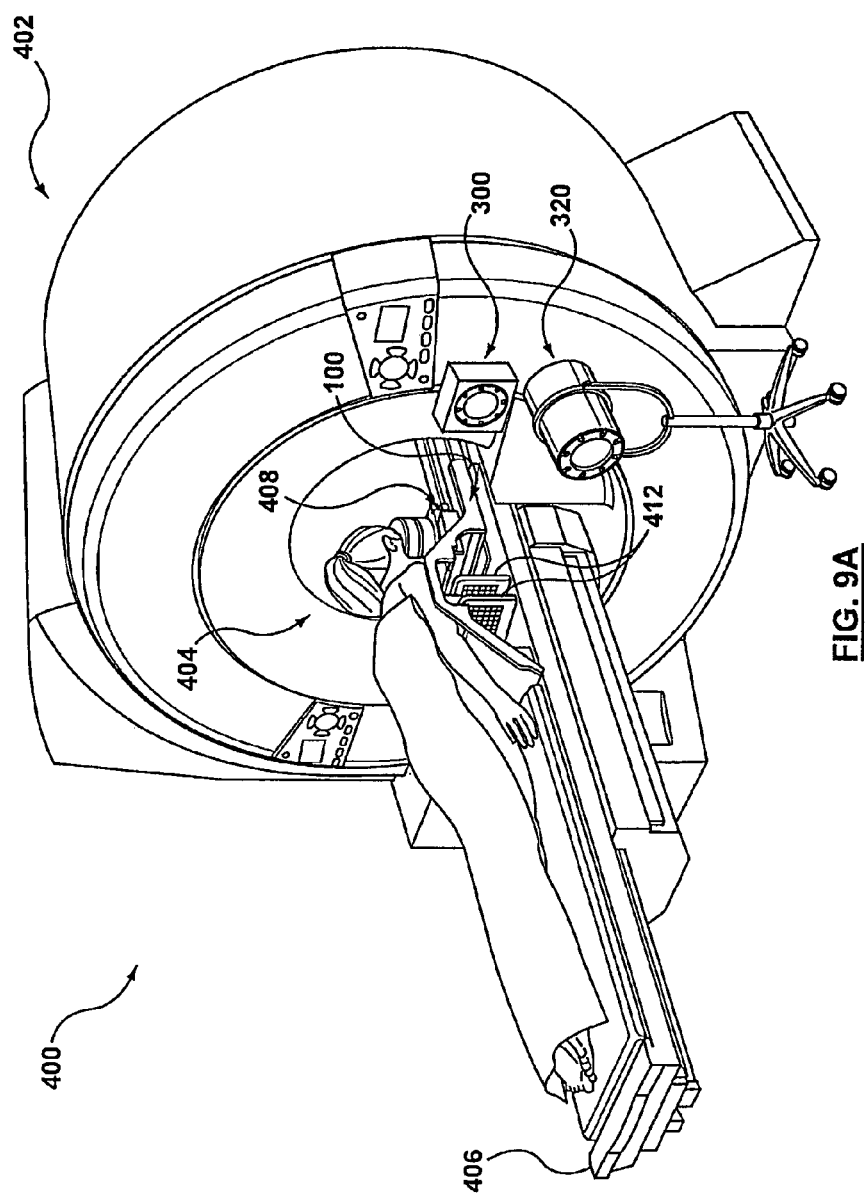
FIG. 9A shows an isometric view of a robotic surgical system including a magnetic resonance imaging (MRI) system in accordance with an example embodiment.
Figure 9B:
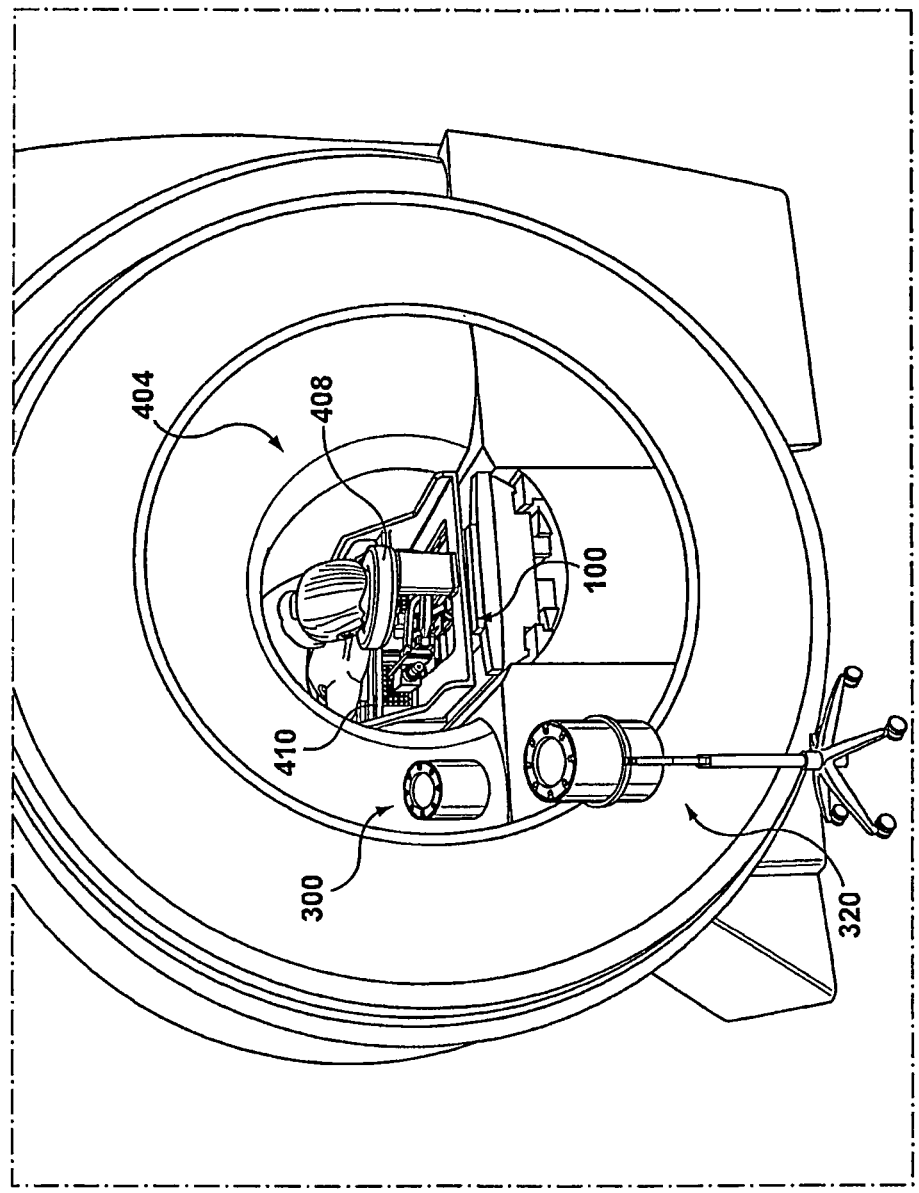
FIG. 9B shows an isometric view of the robotic surgical system shown in FIG. 9A in another mode of operation.

Reference is now made to FIGS. 9A to 9C, which show a robotic surgical system 400 including a magnetic resonance imaging (MRI) system 402 in accordance with an example embodiment. As shown, a breast imaging assembly 404 can be used with a patient support table 406. The patient lies prone on top of the assembly 404 with the sternum resting on a central support beam (not shown). The patient's head is supported by head support 408. The patient's shoulders are supported by shoulder supports 410. The patient's breasts extend down into the breast imaging assembly 404. As shown, the patient may be put into the magnet bore hole of the MRI system 402 head first. Alternatively, the patient may be inserted feet first into the MRI system 402.

The breasts are compressed by compression plates 412, wherein the compression plates 412 may compress the breast either in a head/feet direction or a lateral direction. When compressing, the compression plates 412 act as a breast stabilization mechanism. In other example embodiments, the compression plates 412 can include a plastic plate with a grid of finely-spaced needle guide holes. In the example embodiment shown in FIG. 9A, the compression plates 412 are oriented along the head/feet direction. The compression plates 412 can further include a plastic plate with large rectangular access windows, which is advantageous when used for positioning of the medical instruments 302. In yet further embodiments, a non-compressive stabilization device may be used.

As best shown in FIG. 9C, the medical insertion device 100 can be dimensioned to be positioned in the limited space located between the head support 408 and the patient support table 406, typically having a restricted height as shown.

In an alternate embodiment, the compression plates 412 are oriented along the lateral direction and the medical insertion device 100 is positioned laterally for procedures to be performed outside of the magnet bore hole of the MRI system 402.

The position of the alignment fiducials 113 (FIG. 1B) relative to the tumor is measured or located on the MR images. The appropriate position and/or angle of the medical instrument 102 can then be determined, and the medical instrument 102 is moved to that position and/or angle using the medical insertion device 100. In another example embodiment, a proper needle entry hole can be determined by determining which hole in the compression plate 412 is closest to the desired entry point, as would be understood in the art.

It can be appreciated that the closed geometry RF coils may be used with a plurality of windings, which can interfere with a lateral or medial biopsy approach direction in some existing conventional systems.

Generally, the tip of the biopsy device (or ablative device) may be seen in the image and can be accurately steered towards a suspected lesion location as imaging continues. This will allow adjustments to the trajectory of the biopsy device which are necessary if the lesion location moves for any reason. In the case of ablative therapy, the robotic manipulation system allows the tool to be repositioned as necessary, in-situ, in order to achieve the goals of the intervention. As mentioned, alignment fiducials (not shown) may also be placed onto the medical instrument 102 to assist in registration.

Referring to FIG. 9A, in some example embodiments, the dispenser system 300 can be mounted onto a front of the frame of the MRI system 402. In such embodiments, the medical insertion device 100 can be swung out or otherwise controlled to access the dispenser system 300. In another example embodiment, also shown in FIG. 9A, the dispenser assembly 320 can be rolled and locked into position adjacent to the front of the MRI system 402. In other example embodiments, the dispenser system 300 can be integrated within or attached to the patient support table 406 for dispensing of the various medical instruments 302. In such embodiments, the medical insertion device 100 may, for example, pitch down into the table 406 to obtain or replace the medical instrument 102.

As shown in FIG. 9B, in some example embodiments, the dispenser system 300 can be mounted onto a rear side of the frame of the MRI system 402, for example in the upper mode of dispensing. In another example embodiment, also shown in FIG. 9B, the dispenser assembly 320 can be rolled and locked into position adjacent to the rear side of the MRI system 402.

Figure 10A:
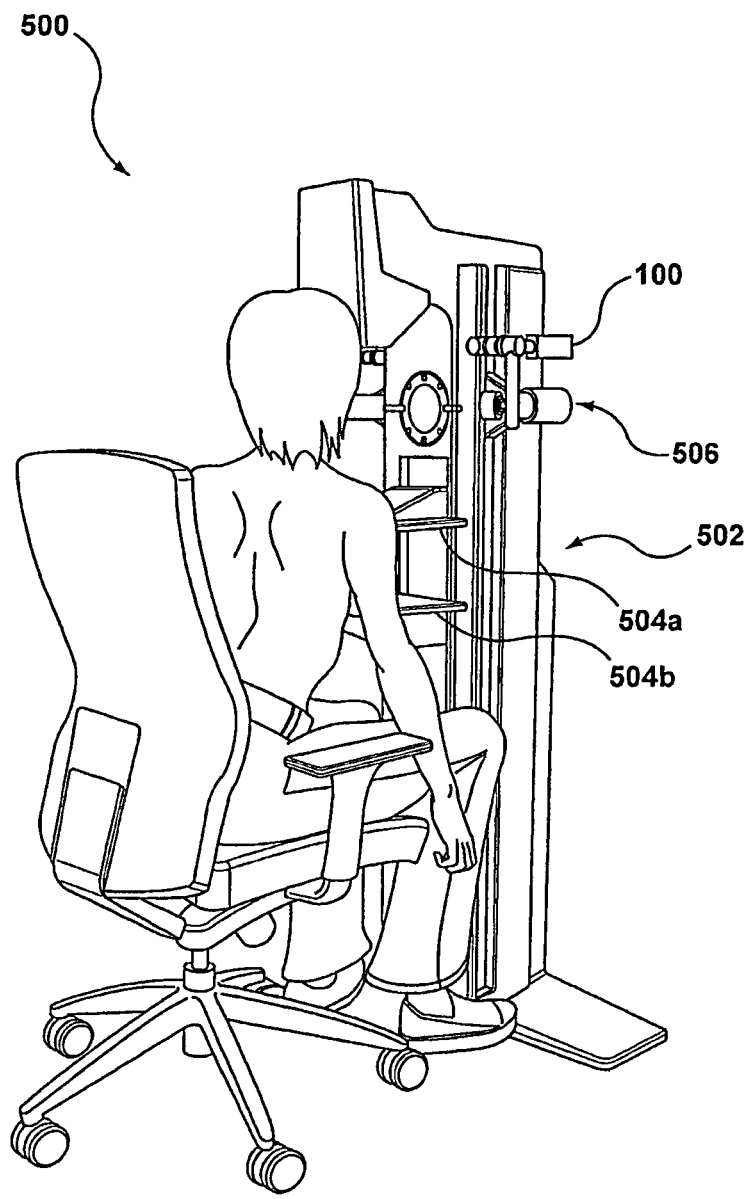
FIG. 10A shows an isometric view of a robotic surgical system including a mammography system in accordance with an example embodiment.
Figure 10B:
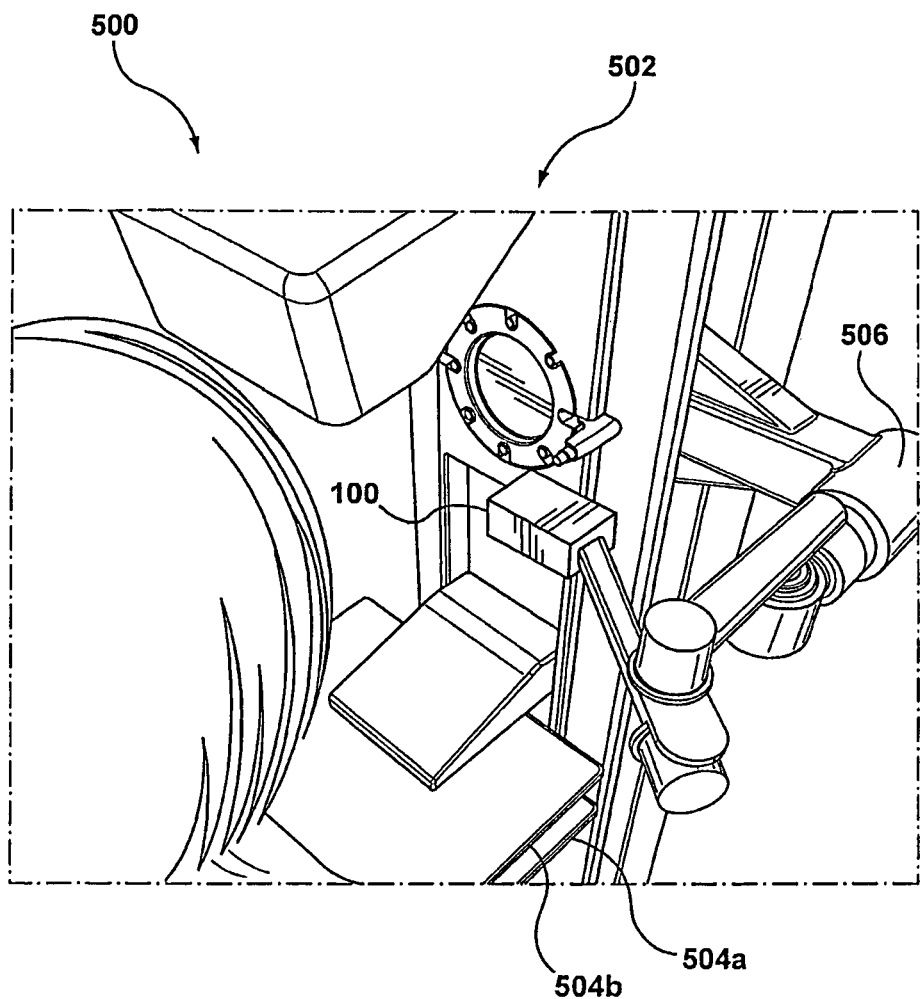
FIG. 10B shows an isometric view of the robotic surgical system shown in FIG. 10A in a dispensing mode of operation.
Figure 10C:
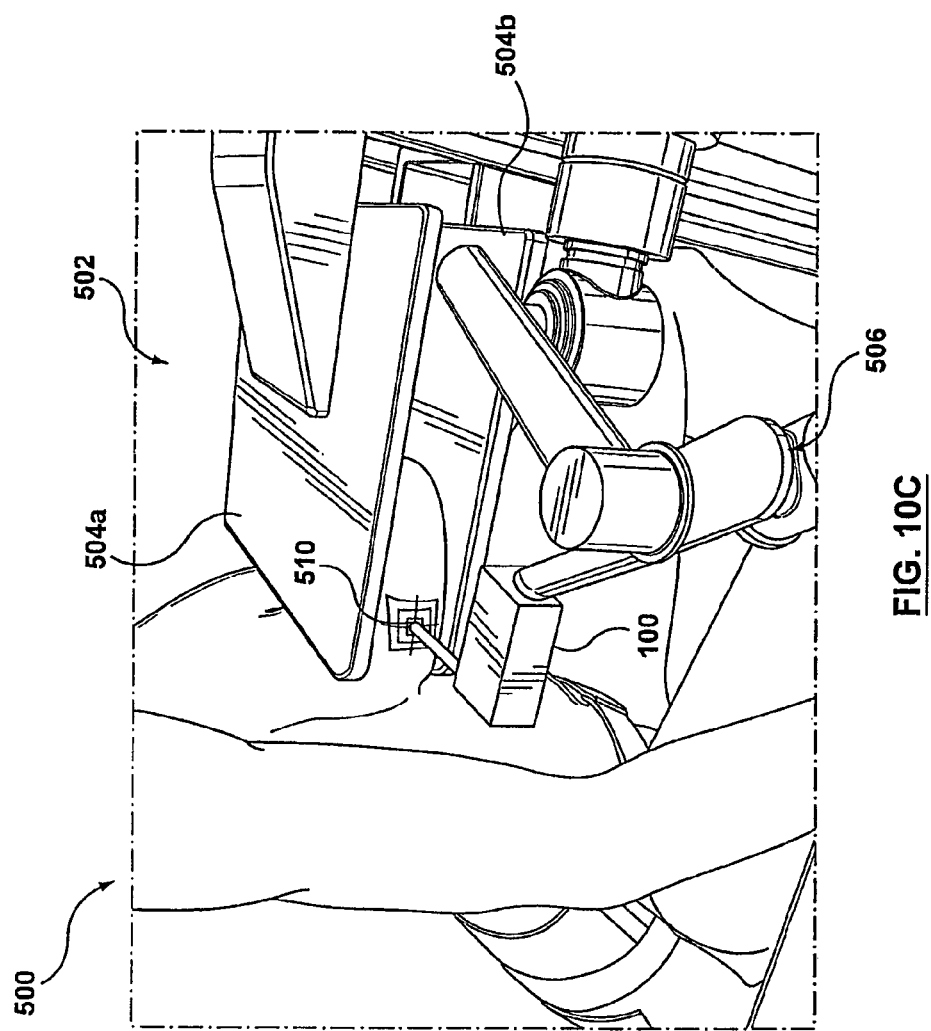
FIG. 10C shows an isometric view of the robotic surgical system shown in FIG. 10A in an insertion mode of operation.

Reference is now made to FIGS. 10A to 10C, which show a robotic surgical system 500 including a mammography system 502 in accordance with an example embodiment. The mammography system 502 can, for example, include an X-Ray based system, an MBI system, or a positron emission mammography (PEM) based system. In PEM/MBI, prior to imaging, an agent is injected into the patient which assists in detection of the lesion. Compression plates 504a, 504b are used to provide stability and immobilization of the breasts. The compression plates 504a, 504b can also include PEM detectors mounted thereon.

As shown in FIG. 10C, there is a limited space in the region transverse to the patient between the compression plates 504a, 504b. In example embodiments, the medical insertion device 100 is dimensioned to fit in this transverse region between the compression plates 504a, 504b. Referring briefly again to FIG. 1A, a height of the drive support plate 114 of the frame 104 can be dimensioned to fit within the transverse space between the compression plates 504a, 504b. In another embodiment (not shown), the medical insertion device 100 is mounted onto the lower compression plate 504b within this transverse region.

As shown, a robotic arm 506 has one end mounted to the mammography system 502 and the other end has the medical insertion device 100 mounted thereon. The robotic arm 506 can, for example, place the medical insertion device 100 between the compression plates 504a, 504b at the appropriate time of the procedure. In other embodiments (not shown), the robotic arm 506 can place the medical insertion device 100 for superior insertion (e.g., from the head) with the compression plates 504a, 504b mounted transversely (for transverse compression) or otherwise suitably modified.

In some example embodiments, as shown in FIG. 10B, the dispenser system 300 can be mounted within the frame of the mammography system 502. In such embodiments, the medical insertion device 100 can controlled or maneuvered to access the dispenser system 300 using the robotic arm 506. In some embodiments, the dispenser system 300 does not rotate but rather the robotic arm 506 is used to retrieve the medical instrument 302 from the appropriate instrument holder 306.

As shown in FIG. 10C, grid marks 510 may be shown in the virtual image to guide the medical insertion device 100 to the target site.

After the core biopsy is performed, the medical insertion device 100 provides an opportunity for other minimally invasive diagnostic procedures and treatments. Examples include: (1) gamma detectors; (2) energized tunneling tips to reduce tunneling forces; (3) inserts to aid in reconstruction of removed tissue (e.g., one or two sided shaver inserts); (4) spectroscopy imaging devices; (5) general tissue characterization sensors {e.g., (a) mammography; (b) ultrasound, sonography, contrast agents, power Doppler; (c) PET and FDG ([Flourine-18]-2-deoxy-2-fluoro-glucose); (d) MRI or NMR, breast coil; (e) mechanical impedance or elastic modulus; (f) electrical impedance; (g) optical spectroscopy, raman spectroscopy, phase, polarization, wavelength/frequency, reflectance; (h) laser-induced fluorescence or auto-fluorescence; (i) radiation emission/detection, radioactive seed implantation; (j) flow cytometry; (k) genomics, PCR (polymerase chain reaction)-brca1, brca2; (l) proteomics, protein pathway}; (6) tissue marker sensing device; (7) inserts or devices for MRI enhancement; (8) bishops on-a-stick; (9) endoscope; (10) diagnostic pharmaceutical agents delivery devices; (11) therapeutic anti-cancer pharmaceutical agents delivery devices; (12) radiation therapy delivery devices, radiation seeds; (13) anti-seeding agents for therapeutic biopsies to block the release of growth factors and/or cytokines (e.g., chlorpheniramine (CPA) is a protein that has been found to reduce proliferation of seeded cancer sells by 75% in cell cultures.); (14) fluorescent tagged antibodies, and a couple fiber optics to stimulate fluorescence from a laser source and to detect fluorescence signals for detecting remaining cancer cells; (15) positive pressure source to supply fluid to the cavity to aid with ultrasound visualization or to inflate the cavity to under the shape or to reduce bleeding; (16) biological tagging delivery devices (e.g., (a) functional imaging of cellular proliferation, neovacularity, mitochondrial density, glucose metabolism; (b) immunohistochemistry of estrogen receptor, her2neu; (c) genomics, PCR (polymerase chain reaction)-brca1, brca2; (d) proteomics, protein pathway); (17) marking clips; (18) mammotome; and (19) obturator trocar; (20) ablative therapies (cryo, RF, laser, etc.).

Figure 11:
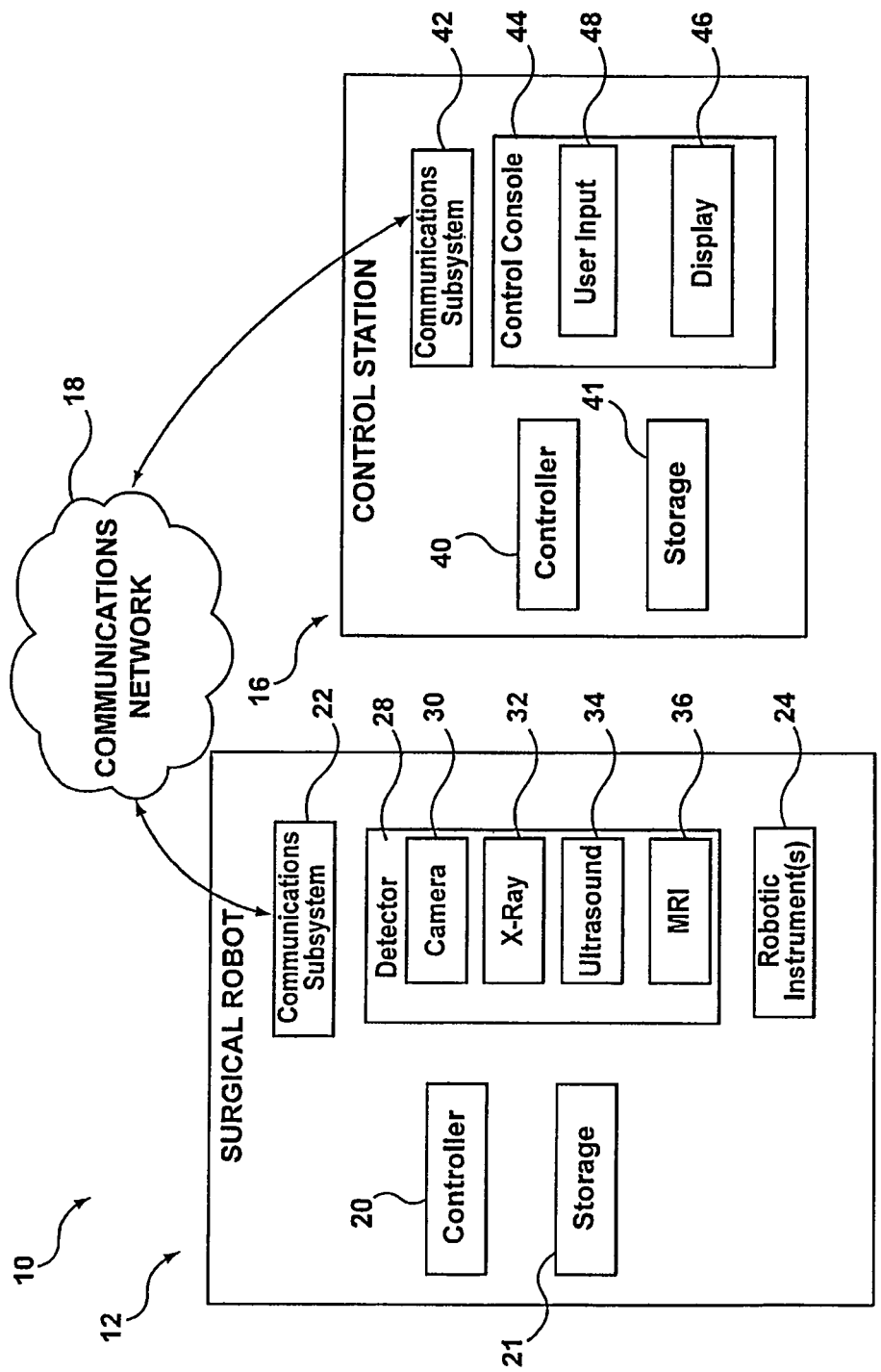
FIG. 11 shows a block diagram of a robotic surgical system in which example embodiments may be applied.

Reference is now made to FIG. 11, which shows a block diagram of a robotic surgical system 10 to which example embodiments may be applied. The system 10 includes a surgical robot 12 for use in a surgical environment. The surgical robot 12 is in communication with a control station 16 either over a communications network 18 (as shown), or via a direct connection. Generally, the surgical robot 12 includes one or more robotic instrument(s) 24 which can be operational in a limited size operating environment defined by an imaging system such as magnetic resonance imaging (MRI). At least one of the robotic surgical instruments 24 may include the medical insertion device 100 as shown in FIG. 1A.

Referring still to FIG. 11, the surgical robot 12 includes a controller 20 for controlling operation of the surgical robot 12, a communications module or subsystem 22 for communicating with the control station 16 over the network 18, and robotic surgical instruments 24 which are controllable by the control station 16 over the network 18. In an example embodiment, the robotic surgical instruments may be haptically controllable which can include force-feedback or touch-feedback control. The controller 20 can include one or more microprocessors or processors that are coupled to a storage 21 (e.g. computer readable storage medium) that includes persistent and/or transient memory. The storage 21 stores information and software enabling the microprocessor(s) of controller 20 to control the subsystems and implement the functionality described herein. The surgical robot 12 includes a detector subsystem 28 for determining spatial information relating to a surgical environment of the surgical robot 12 (including a subject patient) and sending/relaying said information to the control station 16 over the network 18. As shown, in some example embodiments the detector 28 may include a camera 30 (for capturing video and/or audio information), an x-ray system 32, an ultrasound system 34, an MRI 36, or others such as Positron Emission Tomography (PET), Positron Emission Mammography (PEM), CT laser mammography, or a GE™ molecular biological imager. In some example embodiments, the controller 20 is configured to operate or provide a local control loop between at least one of the subsystems and the robotic surgical instruments 24.

Figure 12:
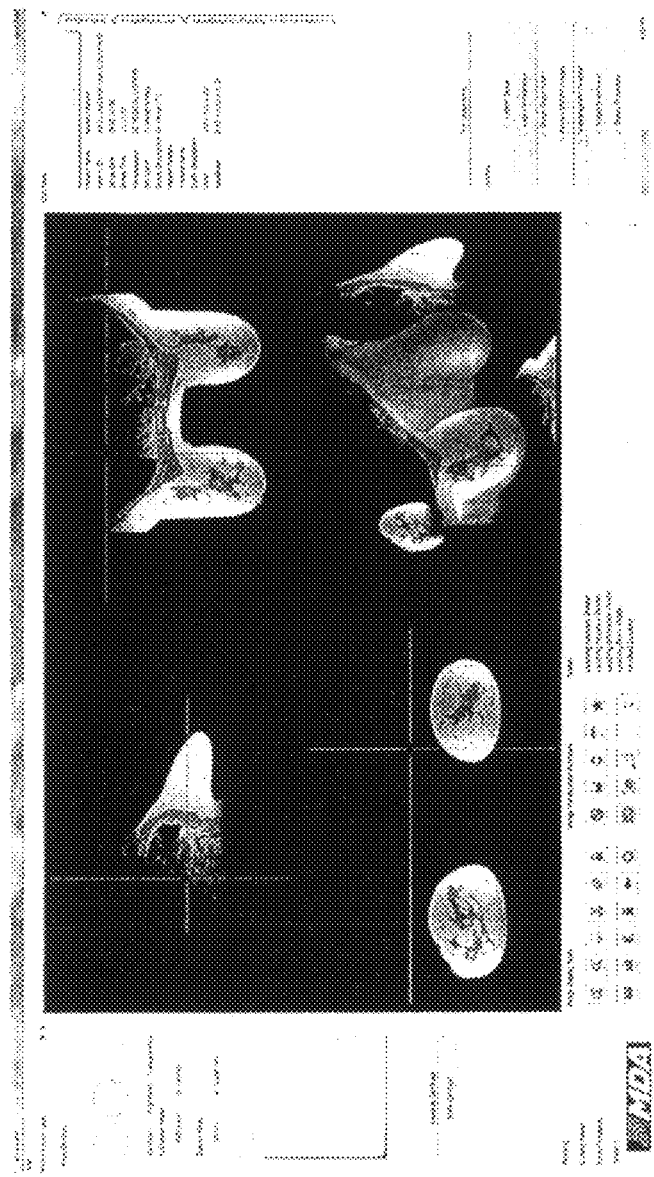
FIG. 12 shows an example interface in accordance with an example embodiment.

The control station 16 includes a controller 40 for controlling operation of the control station 16 and a communications subsystem 42 for communicating with the surgical robot 12 over the network 18. The controller 40 is coupled to a storage 41. A control console 44 provides an interface for interaction with a user, for example a surgeon. The control console 44 includes a display 46 (or multiple displays), and a user input 48. In some embodiments, the user input 48 may further include haptic controllers (not shown) for allowing the user to haptically control the robotic surgical instruments 24 of the surgical robot 12, for example with force-feedback or touch control. Although only one control station 16 is shown, in other embodiments two or more control stations may be used, each configured for controlling at least part of the surgical robot 12. An example interface is shown in FIG. 12, which in example embodiments includes a graphical user interface (GUI) for interfacing with the user.

Generally, the system 10 can be used to perform a procedure by breaking down a procedure into a series of interconnected sub-tasks. Some of the sub-tasks are performed automatically by the surgical robot 12 to control the robotic instruments 24 and the subsystems to perform the particular sub-task. Some of the other sub-tasks are "semi-automated", meaning having some control from the control station 16 as well as some local control from the controller 20.

Each defined sub-task may for example be stored in a storage 21 accessible by the controller 20, the storage 21 including a library. The library includes a sequence of sub-tasks (both automated and "semi-automated"). Specifically, some of the sub-tasks have instructions to automatically control the robotic instruments 24 and the subsystems to perform the sub-task. During automated control, the controller 20 may automatically perform the surgical functions by providing the local control loop with the subsystems. Some of the other sub-tasks may be "semi-automated", meaning having some control from the control station 16 as well as some local automation (with the controller 20 providing local control loops as described herein). During semi-automated control, the control station 16 and the subsystems may be in a master-slave relationship. In example embodiments, such semi-automated control may be configured in an external control loop as between the subsystems and the robotic instruments 24, which are facilitated by the control station 16.

The sub-task may be selectively retrieved from the library and combined into a defined sequence or sequences to perform the surgical procedure. The flow from one sub-task to another is stored in the library. Each sub-task may use imagery and other parameters to verify sub-task completion. In some example embodiments, each of the sub-tasks in a particular entire procedure may be automatically performed by the surgical robot 12.

For example, for a breast biopsy a first sub-task may be the semi-automated positioning of the medical insertion tool 100 by the surgeon in front of the desired insertion region, while the second sub-task may be the automated insertion of the biopsy needle subcutaneously into the target site.

Referring again to FIG. 11, the robotic surgical instruments 24 may include any number or combination of controllable mechanisms. The robotic surgical instruments 24 include end effectors such as grippers, cutters, manipulators, forceps, bi-polar cutters, ultrasonic grippers & probes, cauterizing tools, suturing devices, etc. The robotic surgical instruments 24 generally include small lightweight actuators and components. In some example embodiments, the robotic surgical instruments 24 include pneumatic and/or hydraulic actuators. Such actuators may further assist in providing motion stability, as further described below. In some example embodiments, various lightweight radiolucent materials for robotic arms as well as the range joint torques, forces, frequency response, ROM, weight and size of different actuators to achieve the maximum function in the surgical robot 12. In another example embodiment, the robotic surgical instrument 24 may be configured to include a therapeutic tool utilizing the administration of high intensity focused ultrasound (HIFU) to control haemorrhage and treat solid tumours. Both the HIFU and the ultrasound 34 (for detecting the surgical environment) may be implemented within the same robotic surgical instrument 24.

Referring still to FIG. 11, the detector subsystem 28 will now be described in greater detail. The incorporation of intra-operative image guidance into surgical robotics provides an additional capability to refine the precision of a surgical procedure. Pre-operative diagnostic imagery may be utilized to plan surgical procedures with the assumption that these diagnostic images will represent tissue morphology at the time of surgery. Along with this pre-operative planning, intra-operative imagery may also be used to modify or refine a present surgical procedure or administer minimally invasive treatment such as HIFU ultrasound therapy used to control bleeding.

One aspect of such image-guided surgery in accordance with example embodiments is registering multiple images to each other and to the patient, tracking instruments intra-operatively and subsequently translating this imagery for real time use in the robot space. The incorporation of medical imagery into surgical planning for the system 10 facilitates the identification of a defined work envelope for single or multiple robotic arms. Intra-operative tracking of the position of the robotic surgical instruments 24 within the defined work envelope can be utilized to develop local control loop systems between the detector 28 and the robotic surgical instruments 24 to define keep-out and work within zones for surgical tasks. This data is incorporated into known algorithms developed for collision avoidance of the multiple robotic arms and optimization of the position of instrumentation for completion of the surgical task.

Different technologies that incorporate a physical marker, such as MR, X-Ray, IR (Infrared) markers or RF (Radiofrequency) devices, or chemical markers, may be used for image registration of specific anatomical landmarks for both the intra-operative tracking of the surgical robot 12 in relation to the patient as well as tracking the surgical instrumentation. Image-based registration is less sensitive to calibration and tracking errors as it provides a direct transformation between the image space and the instrument space. The information from anatomical landmarks can be registered with the diagnostic imagery used to plan the surgical procedure and subsequently translated into the robotic space for completion of an image guided surgical procedure. This translation is performed using a registration procedure between the robot and the imaging device. The incorporation of real-time intra-operative tracking of anatomical landmarks provides a mechanism of incorporating compensatory motion of the robotic arm to accommodate patient movement thereby enhancing the precision of the robotic task.

In another example embodiment, the detector subsystem 28 includes the incorporation of image guidance into the robotic surgery, including predetermined marker shapes and positions that provide optimal accuracy for fiducial marker monitoring and tracking of anatomical landmarks, instrument position and the position of the robotic arms under the constraints imposed by the imaging device and the limited volume available in the surgical work envelope.

Imagery can also be incorporated as one of many parameters used to provide local control loop feedback in performing autonomous robotic tasks. In some example embodiments, the control station 16 and the surgical robot 12 operate in a master slave relationship. Such embodiments may incorporate semi-autonomous surgical robotics wherein the surgical robot 12 may autonomously perform some specified surgical tasks that are part of a sequence of a larger task comprising the surgical procedure, for example using a locally controlled loop implemented by the controller 20. This may for example enables the surgeon to selectively perform techniques best undertaken with a master slave relationship while using automated robotics to perform specific tasks that require the enhanced precision of a surgical robot. For example, such tasks may include the precision placement of brachytherapy for cancer treatment or the precision drilling and intra-operative positioning of hardware in orthopaedic surgery.

In another aspect the control station 16 displays diagnostic images, uploaded from a diagnostic workstation (such as CT, MRI, or the like), such that a clinician may select start (insertion point) and end (lesion) location points. A 3D representation of the 2D image slice data with controllable view angle enables the clinician to plan an optimal path avoiding blood vessels and other tissue structures. The avoidance of hematoma can be important with regard to post biopsy image quality for target confirmation.

The control station 16 calculates the linear and angular motions necessary to move the surgical robotic manipulator over the planned trajectory and send appropriate commands to plurality of motors to move the medical instrument.

Referring still to FIG. 11, the communications network 18 may further include a direct wireless connection, a satellite connection, a wide area network such as the Internet, a wireless wide area packet data network, a voice- and data network, a public switched telephone network, a wireless local area network (WLAN), or other networks or combinations of the forgoing.

In one aspect the surgical robot 12 can move the medical instrument 100 while diagnostic images are being acquired. This can reduce the targeting confirmation time can be critical in light of contrast enhancement degradation issues. In addition, targeting errors as a result of lesion motion due to the force of the advancing needle, for example, can also be adjusted with the patient remaining within the magnet bore hole. The automated steering uses targeting software as we as force sensors to prevent accidental excursion into the wrong tissue. The software allows the medical practitioner to plan the full trajectory of the needle or ablation instrument from the skin surface down to the lesion and to steer the medical instrument 100 using real time MR. Again, MR fiducials as well as of MR molecular tagging may also be used to improve targeting accuracy.

In yet another aspect a remote control station 16 can enable control of the robotic instruments 24 from a distance such that an expert in the breast biopsy and ablation procedures will direct the procedure from a distance. The remote control station 16 can connect to one or more local workstations such that one physician may perform procedures at a plurality of remote sites (the master controller is at the remote site). Alternatively, the local workstation may control the procedure and a remote station will monitor the procedure for teaching purposes, for example. Examples of various systems which can use local and remote workstations collaboratively are described in the PCT Patent Application No. WO 2007/121,572, the contents of which are herein incorporated by reference.

In some example embodiments, rather than the breast biopsy or ablative procedures described herein, additional procedures can be performed using several imaging modalities such as MRI, CT, PET, PEM, BSGI, X-ray, or sonography, or other modalities where there is an advantage to accurately target a pathology for biopsy or ablation. It would also be appreciated that in some example embodiments other areas of the body can be targeted other than the breast. Such applications include liver, axilla (sentinel node biopsy), lung, kidney, prostate, uterus, and neurological.

The various example embodiments described as systems would similarly apply to methods, and vice-versa.

Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art, such variations being within the intended scope of the present disclosure. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the described embodiments. The subject matter described herein intends to cover and embrace all suitable changes in technology.

What is claimed is:

1. A robotic system, comprising:
   a) an insertion device comprising:
      a mounting arm;
      a first carriage pivotally connected to a distal portion of the mounting arm;
      a second carriage pivotally connected to the distal portion of the mounting arm;
      a third carriage pivotally connected to a proximal portion of the mounting arm;
      a fourth carriage pivotally connected to the proximal portion of the mounting arm;
      an interface for interfacing with a medical instrument, wherein the interface is slideably connected to the mounting arm; and
      one or more mechanisms configured to effect movement of the interface along a length of the mounting arm in an insertion direction, and to effect pitch and yaw of the mounting arm; and
   b) a controller configured to control the one or more mechanisms for effecting movement of the interface and for effecting pitch and yaw of the mounting arm.

2. The robotic system as claimed in claim 1, wherein the insertion device further comprises:
   a frame;
   a linear slide assembly connected to the frame;

a first slideable connection, wherein the first carriage is slideably connected to the linear slide assembly through the first slideable connection;

a second slideable connection, wherein the second carriage is slideably connected to the linear slide assembly through the second slideable connection; and one or more mechanisms for effecting movement of the first carriage and the second carriage along the linear slide assembly in a direction that is transverse to the insertion direction.

3. The robotic system as claimed in claim 2, wherein the mounting arm or frame comprises a fiducial marker.

4. The robotic system as claimed in claim 2, wherein:
the first carriage is pivotally connected to the mounting arm via a first sway arm; and
the second carriage is pivotally connected to the mounting arm via a first coupling arm.

5. The robotic system as claimed in claim 4, wherein the insertion device further comprises:
a third slideable connection, wherein the third carriage is slideably connected to the linear slide assembly through the third slideable connection;
a fourth slideable connection, wherein the fourth carriage is slideably connected to the linear slide assembly through the fourth slideable connection; and
one or more mechanisms for effecting movement of the third carriage and the fourth carriage along the linear slide assembly in the direction that is transverse to the insertion direction.

6. The robotic system as claimed in claim 5, wherein the linear slide assembly comprises a first track system and a second track system, wherein the first carriage and the second carriage are slideably connected to the first track system and the third carriage and the fourth carriage are slideably connected to the second track system.

7. The robotic system as claimed in claim 6, wherein:
the mounting arm or frame comprises a fiducial marker;
the mounting arm or the interface comprises a force sensor;
movement of each of the first carriage, the second carriage, the third carriage and the fourth carriage along the linear slide assembly is independently controllable.

8. The robotic system as claimed in claim 7, which further comprises c) a detector subsystem for determining spatial information, wherein the controller is in communication with the detector subsystem to receive spatial information.

9. The robotic system as claimed in claim 7, wherein:
the first carriage and the second carriage are configured to slide along a first common guide rail; and
the third carriage and the fourth carriage are configured to slide along a second common guide rail different from the first common guide rail.

10. The robotic system as claimed in claim 5, wherein movement of each of the first carriage, the second carriage, the third carriage and the fourth carriage along the linear slide assembly is independently controllable.

11. The robotic system as claimed in claim 5, wherein the one or more mechanisms for effecting movement of the first carriage, the second carriage, the third carriage and the fourth carriage along the linear slide assembly comprise a rotary drive assembly.

12. The robotic system as claimed in claim 4, wherein:
the third carriage is pivotally connected to the mounting arm via a second sway arm; and
the fourth carriage is pivotally connected to the mounting arm via a first coupling arm.

13. The robotic system as claimed in claim 1, wherein the one or more mechanisms for effecting movement of the interface along a length of the mounting arm in an insertion direction comprise a pneumatic motor, a piezoelectric motor, a vacuum-actuated driver or a hydraulic driver.

14. The robotic system as claimed in claim 1, wherein the interface is configured for interfacing with the medical instrument wherein the medical instrument is oriented in the insertion direction or wherein the medical instrument is oriented in a direction opposite to the insertion direction.

15. The robotic system as claimed in claim 1, wherein the interface is for interfacing with a medical instrument that is a biopsy tool, an ablation tool, a needle, a probe, an ultrasound probe, a fiber optic probe, a magnetic resonance imaging (MRI) coil or an end effector.

16. The robotic system as claimed in claim 1, wherein the mounting arm or the interface comprises a force sensor.

17. The robotic system as claimed in claim 1, which further comprises c) a detector subsystem for determining spatial information, wherein the controller is in communication with the detector subsystem to receive spatial information.

18. The robotic system as claimed in claim 17, wherein the detector subsystem comprises a camera, an X-ray system, a computed tomography system, a mammography system, a laser-induced fluorescence or auto-fluorescence system, an optical spectroscopy system, an ultrasound system, a magnetic resonance imaging (MRI) system, a positron emission tomography (PET) system, a positron emission mammography (PEM) system, a molecular breast imaging (MBI) system, a computed tomography (CT) laser mammography system, a molecular biological imager, a breast specific gamma imaging (BSGI) system or a sonography system.

19. The robotic system as claimed in claim 1, which further comprises d) a dispenser system, wherein the dispenser system comprises:
a dispenser frame defining or including at least one instrument holder for holding and releasably providing the medical instrument to the interface, wherein the at least one instrument holder is arranged on the dispenser frame around a centre of rotation of the dispenser frame; and
a rotating mechanism for rotating the dispenser frame around the centre of rotation.

* * * * *